US009241718B2

(12) United States Patent
Plaza et al.

(10) Patent No.: US 9,241,718 B2
(45) Date of Patent: Jan. 26, 2016

(54) DELIVERY AND DETACHMENT SYSTEMS AND METHODS FOR VASCULAR IMPLANTS

(71) Applicant: Sequent Medical, Inc., Aliso Viejo, CA (US)

(72) Inventors: Claudio Plaza, Irvine, CA (US); Scott Hemmelgarn, Lake Forest, CA (US); Eileen Charlton, Garden Grove, CA (US); Todd Hewitt, Laguna Niguel, CA (US); Philippe Marchand, Munich (DE); Daniel Welsh, Encinitas, CA (US); William R. Patterson, Irvine, CA (US); Son Pham, Garden Grove, CA (US)

(73) Assignee: Sequent Medical, Inc., Aliso Viejo, CA (US)

( * ) Notice: Subject to any disclaimer, the term of this patent is extended or adjusted under 35 U.S.C. 154(b) by 20 days.

(21) Appl. No.: 14/491,688

(22) Filed: Sep. 19, 2014

(65) Prior Publication Data

US 2015/0012033 A1    Jan. 8, 2015

Related U.S. Application Data

(63) Continuation of application No. 14/093,826, filed on Dec. 2, 2013, now Pat. No. 8,876,855, which is a continuation of application No. 13/842,492, filed on Mar. 15, 2013, now Pat. No. 8,597,323.

(60) Provisional application No. 61/727,257, filed on Nov. 16, 2012.

(51) Int. Cl.
*A61M 29/00* (2006.01)
*A61B 17/12* (2006.01)

(52) U.S. Cl.
CPC ..... *A61B 17/12113* (2013.01); *A61B 17/12109* (2013.01); *A61B 17/12172* (2013.01); *A61B 2017/12068* (2013.01); *A61B 2017/12077* (2013.01)

(58) Field of Classification Search
CPC ............... A61B 17/12113; A61B 17/12022; A61B 2017/12068; A61B 17/12172; A61B 17/12109; A61B 2017/12077; A61B 17/12145; A61B 17/12154; A61B 17/1214; A61B 2017/12054; A61B 2017/12063; A61F 2002/9505
USPC ................. 606/108, 191, 194, 200; 623/1.11
See application file for complete search history.

(56) References Cited

U.S. PATENT DOCUMENTS

| 4,346,712 A | 8/1982 | Handa et al. |
| 4,402,319 A | 9/1983 | Handa et al. |

(Continued)

FOREIGN PATENT DOCUMENTS

JP    52141092    11/1977

OTHER PUBLICATIONS

Notice of Allowance dated Sep. 11, 2013 from USPTO for related U.S. Appl. No. 13/842,492.

(Continued)

*Primary Examiner* — Katherine M Shi
(74) *Attorney, Agent, or Firm* — Klein, O'Neill & Singh, LLP

(57) ABSTRACT

A system for delivering an implant device to a vascular site in a patient a delivery pusher apparatus, an implant device detachably connected to the delivery pusher apparatus by a tether having a distal end connected to a proximal end of the implant device, wherein the tether is substantially non-tensioned when connecting the implant device to the delivery pusher, and an electrical heating element configured coaxially around at least a portion of the tether, wherein heat generated by the heating element severs the tether at a point near the proximal end of the implant device.

20 Claims, 15 Drawing Sheets

(56) References Cited

U.S. PATENT DOCUMENTS

| | | | |
|---|---|---|---|
| 5,108,407 A | 4/1992 | Geremia et al. | |
| 5,122,136 A | 6/1992 | Guglielmi et al. | |
| 5,569,245 A | 10/1996 | Guglielmi et al. | |
| 5,578,074 A | 11/1996 | Mirigian | |
| 5,759,161 A | 6/1998 | Ogawa et al. | |
| 5,944,733 A | 8/1999 | Engelson | |
| 5,984,929 A | 11/1999 | Bashiri et al. | |
| 5,989,242 A | 11/1999 | Saadat et al. | |
| 6,093,199 A | 7/2000 | Brown et al. | |
| 6,156,061 A | 12/2000 | Wallace et al. | |
| 6,159,206 A | 12/2000 | Ogawa | |
| 6,165,178 A | 12/2000 | Bashiri et al. | |
| 6,277,126 B1 | 8/2001 | Barry et al. | |
| 6,296,622 B1 | 10/2001 | Kurz et al. | |
| 6,425,914 B1 | 7/2002 | Wallace et al. | |
| 6,468,266 B1 | 10/2002 | Bashiri et al. | |
| 6,478,773 B1 | 11/2002 | Gandhi et al. | |
| 6,500,149 B2 | 12/2002 | Gandhi et al. | |
| 6,607,539 B1 | 8/2003 | Hayashi et al. | |
| 6,743,236 B2 | 6/2004 | Barry et al. | |
| 6,743,251 B1 | 6/2004 | Eder | |
| 6,835,185 B2 | 12/2004 | Ramzipoor et al. | |
| 6,953,473 B2 | 10/2005 | Porter | |
| 6,966,892 B2 | 11/2005 | Gandhi et al. | |
| 7,179,276 B2 | 2/2007 | Barry et al. | |
| 7,182,774 B2 | 2/2007 | Barry et al. | |
| 7,198,613 B2 | 4/2007 | Gandhi et al. | |
| 7,316,706 B2 | 1/2008 | Bloom et al. | |
| 7,575,582 B2 | 8/2009 | Gandhi et al. | |
| 7,578,826 B2 | 8/2009 | Gandhi et al. | |
| 7,722,637 B2 | 5/2010 | Barry et al. | |
| 8,182,506 B2 | 5/2012 | Fitz et al. | |
| 8,192,480 B2 | 6/2012 | Tieu et al. | |
| 2002/0183787 A1 | 12/2002 | Wahr et al. | |
| 2004/0172053 A1 | 9/2004 | Barry et al. | |
| 2004/0220563 A1 | 11/2004 | Eder | |
| 2005/0113864 A1 | 5/2005 | Gandhi et al. | |
| 2005/0149108 A1 | 7/2005 | Cox | |
| 2005/0154401 A1 | 7/2005 | Weldon et al. | |
| 2005/0267511 A1 | 12/2005 | Marks et al. | |
| 2006/0052815 A1 | 3/2006 | Fitz et al. | |
| 2006/0116708 A1 | 6/2006 | Ogawa et al. | |
| 2006/0200192 A1 | 9/2006 | Fitz et al. | |
| 2006/0212055 A1 | 9/2006 | Karabey et al. | |
| 2006/0247618 A1 | 11/2006 | Kaplan et al. | |
| 2006/0271086 A1 | 11/2006 | Ramzipoor et al. | |
| 2007/0106323 A1 | 5/2007 | Barry et al. | |
| 2007/0167911 A1 | 7/2007 | Gandhi et al. | |
| 2008/0228215 A1 | 9/2008 | Strauss et al. | |
| 2009/0062812 A1 | 3/2009 | Fitz et al. | |
| 2009/0275974 A1 | 11/2009 | Marchand et al. | |
| 2010/0114085 A1 | 5/2010 | Thompson et al. | |
| 2010/0160944 A1* | 6/2010 | Teoh | A61B 17/12022 606/191 |
| 2010/0268204 A1 | 10/2010 | Tieu et al. | |
| 2014/0277092 A1 | 9/2014 | Teoh et al. | |
| 2014/0277093 A1 | 9/2014 | Guo et al. | |
| 2014/0277094 A1 | 9/2014 | Chen et al. | |

OTHER PUBLICATIONS

Notice of Allowance dated Aug. 13, 2014 from USPTO for related U.S. Appl. No. 14/093,826.

International Search Report from Korean Intellectual Property Office dated Jan. 22, 2014 for related International Application No. PCT/US2013/066687.

Written Opinion from Korean Intellectual Property Office dated Jan. 22, 2014 for related International Application No. PCT/US2013/066687.

* cited by examiner

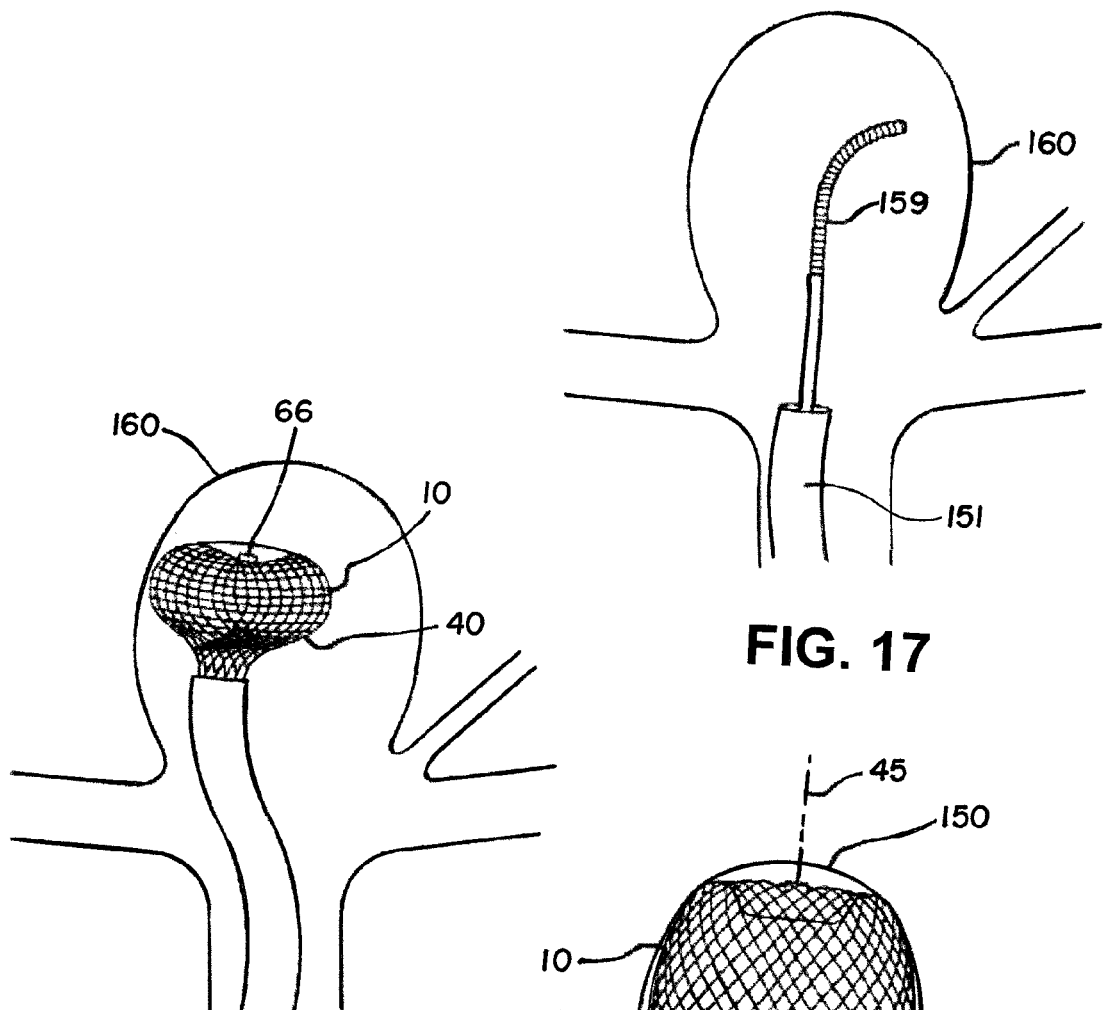
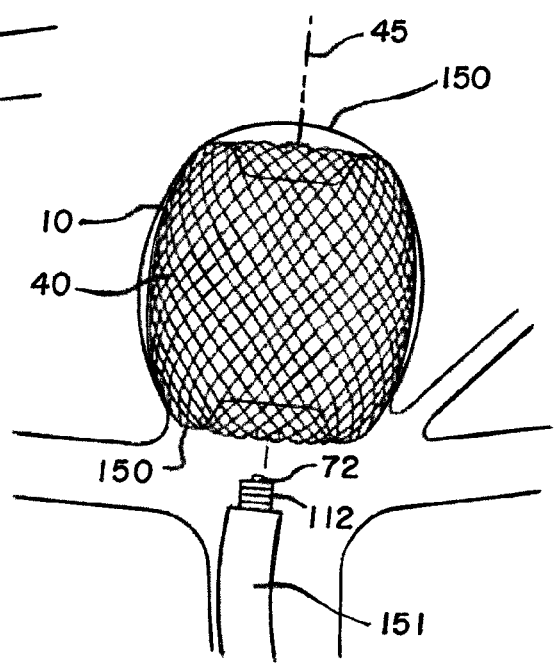
FIG. 17
FIG. 18
FIG. 19

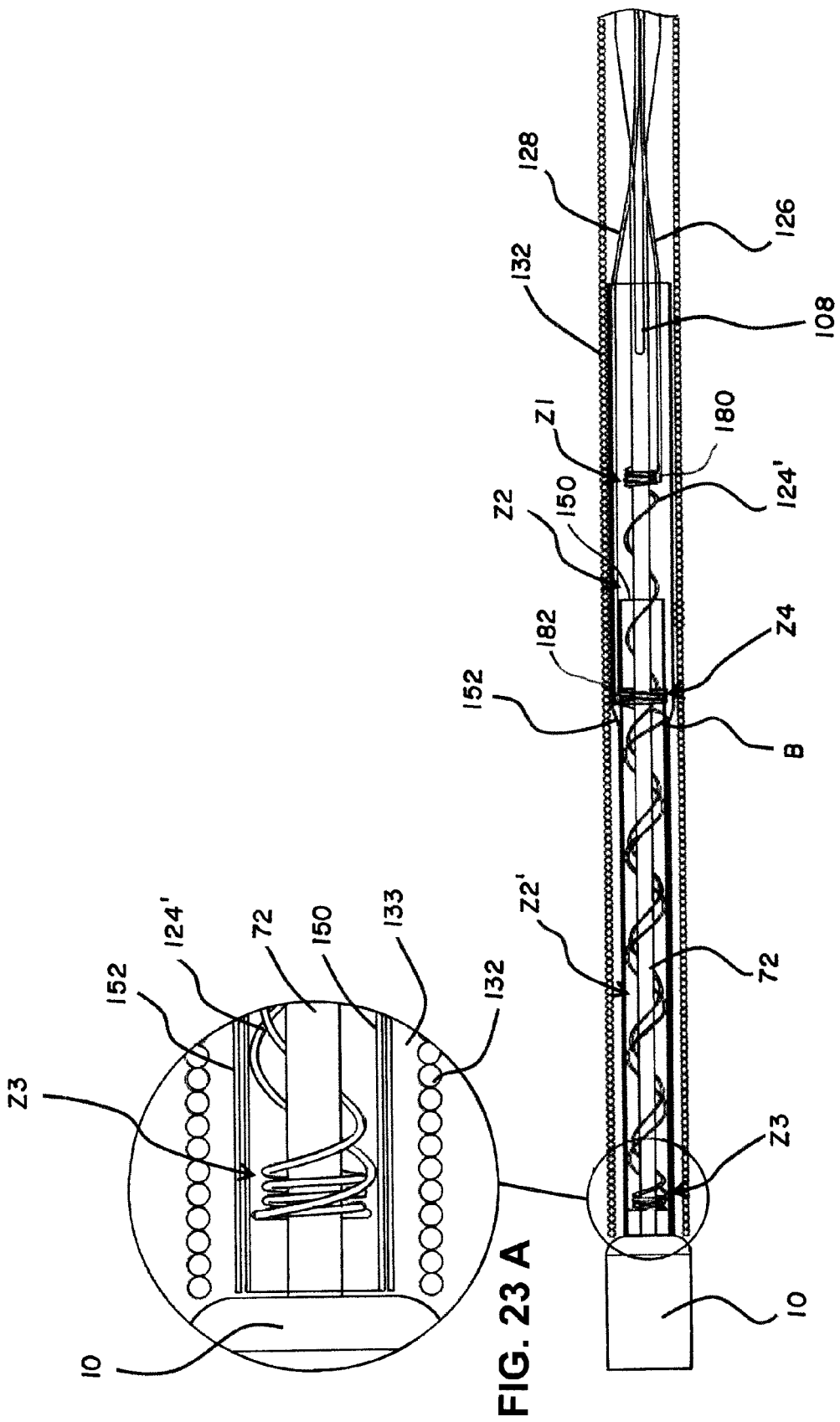

DELIVERY AND DETACHMENT SYSTEMS AND METHODS FOR VASCULAR IMPLANTS

CROSS REFERENCE TO RELATED APPLICATIONS

This patent application is a continuation of U.S. application Ser. No. 14/093,826 filed on Dec. 2, 2013; which is a continuation of U.S. application Ser. No. 13/842,492 filed Mar. 15, 2013, now U.S. Pat. No. 8,597,323; which claims the benefit under 35 U.S.C. §119(e) of U.S. Provisional Application Ser. No. 61/727,257, filed on Nov. 16, 2012. The disclosures of the aforementioned applications are incorporated herein by reference in their entireties.

BACKGROUND

The use of catheter delivery systems for positioning and deploying therapeutic devices, such as balloons, stents and embolic devices, in the vasculature of the human body has become a standard procedure for treating endovascular diseases. It has been found that such devices are particularly useful in treating areas where traditional operational procedures are impossible or pose a great risk to the patient, for example in the treatment of aneurysms in intracranial blood vessels. Due to the delicate tissue surrounding intracranial blood vessels, especially for example brain tissue, it is very difficult and often risky to perform surgical procedures to treat defects of intracranial blood vessels. Advancements in catheter deployment systems have provided an alternative treatment in such cases. Some of the advantages of catheter delivery systems are that they provide methods for treating blood vessels by an approach that has been found to reduce the risk of trauma to the surrounding tissue, and they also allow for treatment of blood vessels that in the past would have been considered inoperable.

Typically, these procedures involve inserting the distal end of a delivery catheter into the vasculature of a patient and guiding it through the vasculature to a predetermined delivery site. A vascular occlusion device may be attached to the end of a delivery member which pushes the occlusion device through the catheter and out of the distal end of the catheter into the delivery site. Some of the problems that have been associated with these procedures relate to the accuracy of occlusion device placement. For example, the force employed to effect detachment of the occlusion device from the delivery member may cause the occlusion device to over shoot the predetermined site or dislodge previously deployed occlusion devices. Also, once the occlusion device is pushed out of the distal end of the catheter it is advantageous for the occlusion device to be retrievable if repositioning or removal is needed. With current electro-thermal detachment systems, there have been instances where the tether members become reconnected to heating elements resulting in non-detachment. Non-detachment can result in adverse clinical complications particularly if multiple devices and being deployed. Premature detachment has also occurred in prior systems which can result in improper placement of a device and distal embolization which can cause and embolic stroke or other adverse clinical consequences.

Numerous devices and release mechanisms have been developed in an attempt to create delivery systems which provide both control of an occlusion device after the device has exited the delivery catheter and a rapid release or detachment mechanism to release the device once the occlusion device is in place with minimal or no force imparted to the implant. Further, there is a need to provide a system that has high reliability with low rates of both non-detachment and premature detachment. With some existing vascular release systems there is the potential to release undesirable particles of materials into the bloodstream that can also cause embolization in the bloodstream. There is therefore a need for a precise method of deploying therapeutic interventional devices without compromising the position of the implant, without causing thermal damage to surrounding tissues, and without releasing undesirable particles of materials into the bloodstream and risking the formation of emboli in the bloodstream.

SUMMARY

The present disclosure provides for an apparatus for deployment of a detachable diagnostic or therapeutic implant device such as a stent, embolic coil or other vascular occlusion device using a catheter by connecting the device to a distal portion of a pusher member. In one presently preferred embodiment, the implant device is detachably mounted to the distal portion of the pusher member by a tubular collar that can be heated by a heater to expand the collar and release and deploy the implant device. In some embodiments, the implant device is detachably mounted to the distal portion of the pusher member by a connector thread or fiber passing through a heating element provided for heating and breaking the connector fiber to release the device. In one presently preferred aspect, the heater element is advantageously contained substantially within the distal portion of the pusher member, which provides a sufficient amount of thermal insulation to minimize the potential for thermal damages of surrounding tissues during detachment, and since the connecting fiber is heated and broken at a location fully contained within the distal portion of the pusher member, the potential for releasing undesirable particles of materials into the bloodstream and consequent embolization in the bloodstream is also minimized.

Some embodiments accordingly provide for an apparatus for release and deployment of a device within the vasculature of a patient, comprising an elongated, flexible delivery or "pusher" apparatus pusher having an interior lumen; a flexible elongate cylindrical core member coaxially within the pusher member; a tether member connecting the pusher member to the implant; and a heating element for severing said tether member. In some embodiments, the device may be designed to be progressively flexible for placement of the therapeutic device within tortuous vasculature, such as the cerebral vasculature. In some embodiments, the heating element may comprise a coil of electrically conductive material such as tungsten, platinum, nickel, titanium, stainless steel (and the various alloys in their various compositions—Pt 8% W, Pt 10% Ir, NiTi (50/50 and others) and Nickel-Chromium alloys. In some embodiments, the heating element coil may have a coating or covering. In some embodiments, the coating or covering may be polyimide and at least about 0.025 mm thick. In some embodiments, the heating element may be configured coaxially about a segment of the tether. In some embodiments the heating element may have an outer tubular shield member to insulate external fluids and tissue and to concentrate the heat to the tether member. Further thermal insulation is provided by a gap of at least about 0.10 mm between the distal end of the heater coil and the proximal end of the implant device. In some embodiments, this gap is between about 0.13 mm 0.20 mm. In some embodiments, the delivery or pusher apparatus may include a portion that is formed as a coil to provide flexibility and bending strain relief in the region of the heating element.

In some embodiments, the heating element may comprise an electrical heater coil that is electrically connectable to a power supply and control unit (which may be combined in a single unit) to supply electrical current to the heater coil. In some embodiments, the heater coil may have a specific heat-generating zone having between 2 and 10 windings or coils. In some embodiments, the heat-generating zone may have between 4 and 8 winds or coils, such as, for example, 3 to 5 winds or coils. The coils in the relatively small heat-generating zone concentrate the heat in a narrow region of the tether member and thus minimize the risk of melted tether material becoming engaged or adhered to the heating element. Thus, the small heating zone may provide a very localized, knife-like severing of the tether. The risk of getting tether material engaged in the heater coil is further reduced by having the distal-most winding continuously wound back on top of itself, allowing the distal-most winding to be an active part of the heating coil. By having the distal-most winding as part of the heat-generating zone of the coil, the melting portion of the tether is shifted beyond the coil, thereby substantially preventing any melted tether material from sticking to the coil. In some embodiments, the tether may be severed close to the connection to the implant device so that little or none of the tether protrudes from the implant after detachment. A heat-generating zone with few coils may reduce the risk of non-detachment. In some embodiments, the heat-generating zone which achieves a temperature sufficient to sever the tether member may have a length that is between about 0.10 mm and about 0.5 mm, for example, between about 0.12 mm and about 0.25 mm. A short or narrow heat-generating zone may allow the tether to be cleanly severed even if it is not under tension (that is, without pre-tensioning) and with low risk of engagement of the tether to the heating element. In some embodiments, electrical supply or lead wires may be connected to the heating element at a point along the external surface of a heating element coil such that the lead wires are generally parallel with the axis of the coils of the heating element. In some embodiments, a lead wire may be connected to one individual heating element coil, and in some embodiments between 1 and 4 coiled heating elements that have been joined together by soldering or welding.

To minimize the rate of non-detachments due to insufficient heat generation and poor or no melting of the polymer tether connecting the implant device to the delivery or pusher apparatus, in some embodiments, the system is configured to maximize the electrical power to the heating element by matching or nearly matching the electrical resistances of the heating coil and conducting electrical wires.

In some embodiments, the tether may be a string, thread, wire, filament, fiber, or the like. Generically this is referred to as the tether. The tether may be in the form of a monofilament, rod, ribbon, hollow tube, or the like. Many materials can be used to detachably join the implant device to the pusher or delivery apparatus. The tether may be joined to the implant device and/or the pusher by welding, potting, knot tying, soldering, adhesive bonding, or other means known in the art.

The present disclosure also relates to methods for deployment and release of a diagnostic or therapeutic implant device within the vasculature of a patient, wherein an implant device is provided that is configured to be placed within the vasculature of a patient; an elongated, flexible pusher or delivery apparatus is provided, having an interior lumen and a heating element; wherein the pusher or delivery apparatus is detachably connected to the implant device by a tether; the implant device and the pusher or delivery apparatus are advanced through a tubular access device such as a microcatheter; the implant device is positioned at a desired placement within a patient's vasculature; and the tether is heated by the heating element until the tether is severed, thereby detaching and deploying the implant device from the flexible pusher or delivery apparatus. In some aspects of the method, the step of heating the tether member comprises passing electrical current through the electrical resistance heater element using DC current until the tether material melt temperature is reached.

When detachment of the implant device at the target site is desired, the operator applies energy to the heating element by way of the electrical lead wires. The electrical power source for the energy may be any suitable source, such as, e.g., a wall outlet, a capacitor, a battery, and the like. In some embodiments of this method, electricity with a potential in the range of 10 volts to 40 volts may be used to generate a current of 1 milliamp to 200 milliamps, depending on the resistance of the system.

In another embodiment, the heating element is heated by light energy, preferably laser light. In such an embodiment, the pusher member includes a fiber optic cable in a lumen thereof for transmitting light from a laser light source (not shown) to a heating element. The heating element receives the light energy, and transforms it into heat energy, which is then transmitted to the tether member until its melting temperature is reached. As a result, the tether is severed and the implant device is disengaged from the pusher member.

BRIEF DESCRIPTION OF THE DRAWINGS

FIGS. 17-19 show deployment sequences of the implant device of FIG. 2 for treatment of a patient's vasculature.

FIG. 23 is an elevation view, partially in cross-section, showing the distal portion of the delivery apparatus and the heater coil therein.

FIG. 23A is a detailed view of the portion of FIG. 23 enclosed within the broken outline 23A.

DETAILED DESCRIPTION

Figure 1:
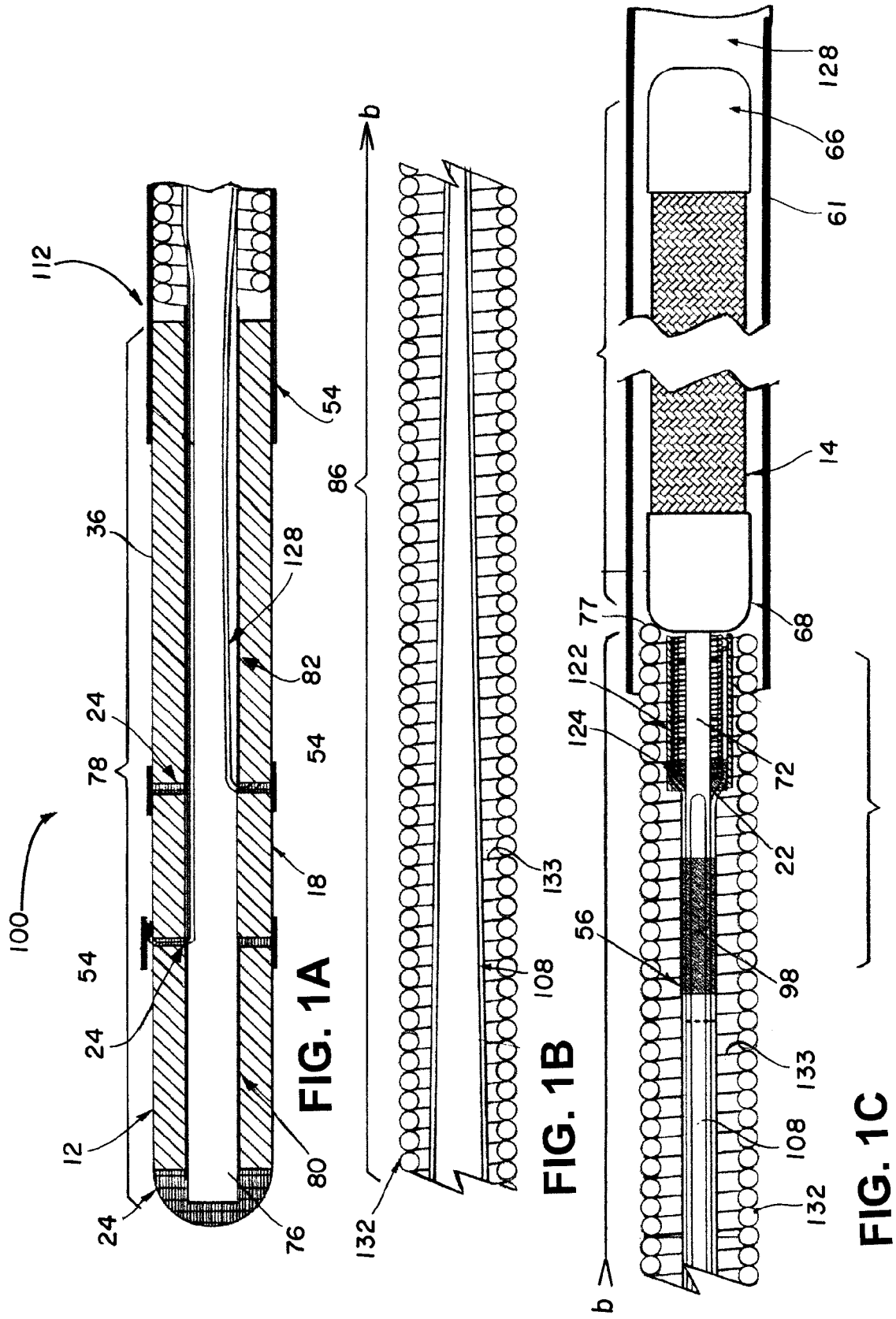
FIGS. 1A, 1B, and 1C together are an elevation view in partial section of an embodiment of a delivery system including a delivery apparatus and a microcatheter for deployment of an implant device for treatment of a patient's vasculature.

Discussed herein are vascular implant devices and methods for using such devices in the treatment of vascular defects, wherein the implant devices are suitable for minimally invasive deployment within a patient's vasculature, and particularly within the cerebral vasculature of a patient. For such embodiments to be effectively delivered to a desired treatment site and effectively deployed, some implant device embodiments may be configured to collapse to a low profile, constrained state with a transverse dimension suitable for delivery through an inner lumen of a microcatheter and deployed from a distal end of a delivery apparatus. Embodiments of these implant devices, once deployed, may also maintain a clinically effective configuration with sufficient mechanical integrity so as to withstand dynamic forces within a patient's vasculature over time that may otherwise result in compaction of a deployed device. It may also be desirable for some implant device embodiments to acutely occlude a vascular defect of a patient during the course of a procedure in order to provide more immediate feedback regarding the success of treatment to the treating physician.

Some embodiments of the implant devices may be particularly useful for the treatment of cerebral aneurysms by reconstructing a vascular wall so as to wholly or partially isolate a vascular defect from a patient's blood flow. Some embodiments may be configured to be deployed within a vascular defect to facilitate reconstruction, bridging of a vessel wall or both in order to treat the vascular defect. For some of these embodiments, one or more layers of the implant device may be configured to anchor or fix the implant device in a clinically beneficial position. For some embodiments, the implant device may be disposed in whole or in part within the vascular defect in order to anchor or fix the device with respect to the vascular structure or defect. The one or more layers of the implant device may be configured to span an opening, neck or other portion of a vascular defect in order to isolate the vascular defect, or a portion thereof, from the patient's nominal vascular system in order to allow the defect to heal or to otherwise minimize the risk of the defect to the patient's health.

Some embodiments of a delivery system for deployment of an implant device to treat a patient's vasculature include a microcatheter having an inner lumen extending the length thereof. The inner lumen provides a passageway for an implant device to treat a patient's vasculature. Some implant device embodiments may include one or more self-expanding resilient layers of thin coupled filaments, the layers defining a longitudinal axis between a proximal end and a distal end. Such embodiments can assume a radially-constrained, axially-elongated state configured for delivery through a microcatheter, with the thin woven filaments extending longitudinally from the proximal end to the distal end being radially adjacent to each other. The delivery system further includes an elongated delivery apparatus having a proximal end and a distal end releasably secured to a proximal portion (e.g., a hub or the like) of the implant device.

FIGS. 1A, 1B, and 1C show a partial sectional view of an embodiment of a delivery system 100 for deploying an implant device to treat a patient's vasculature. The delivery system 100 may include a microcatheter 61 and a delivery apparatus 112 along with an implant device 10. The delivery apparatus 112 and the implant device 10 may be configured to be deployed via the microcatheter 61. The delivery apparatus or delivery "pusher" 112 has a center portion 86 comprising a flexible over-coil 132, defining an axial lumen 133. The over-coil 132 coaxially surrounds an elongated flexible pusher body that extends axially through the coil lumen 133 between a proximal end 76 and a distal end 77 of the delivery apparatus 112. In the illustrated embodiment, the flexible pusher body includes a core wire 108. Alternatively, the pusher body 108 may be a tube (not shown)

A proximal engagement portion 78 may be attached to a proximal end of the center portion 86 by a tubular member such as a first shrink tubing 54. The proximal engagement portion 78 may be formed from three metallic handle segments, a proximal handle segment 12, a middle handle segment 18, and a distal handle segment 36. The handle segments may be joined together with an insulating first adhesive 24. A length of the first shrink tubing 54 may be shrunk onto a distal end of the handle and a proximal end of the over-coil 132, coupling or mechanically securing them together. Shorter lengths of the shrink tubing 54 may be shrunk over places where the segments are joined together.

Outside surfaces of the handle segments may serve as circumferential electrical contacts. A first lead wire 126 may be coupled to the middle handle segment 18. A second lead wire 128 may be coupled to the distal handle segment 36. A first length of tubing 80, such as polyimide tubing may be employed to line the inside of the proximal handle segment 12. A second length of tubing 82, such as polyimide tubing, may be disposed to line the inside of the distal handle segment 36. The core wire 108 may be disposed inside the over-coil 132 of the delivery apparatus 112, and its proximal end may be secured to the proximal end of the handle 78 with the first adhesive 24. A detachment device 124, which in the disclosed embodiments is a heater coil, may be formed inside a distal section 118 of the delivery apparatus 112. The heater coil 124 is advantageously oriented coaxially with the longitudinal axis of the delivery apparatus 112, thereby allowing for a smaller delivery profile compared to non-coaxial arrangements. The implant device 10 may be detachably affixed to the delivery apparatus 112 by a tether 72, with detachment effected by severing the tether using the detachment device, e.g., the heater coil 124.

Figure 2:
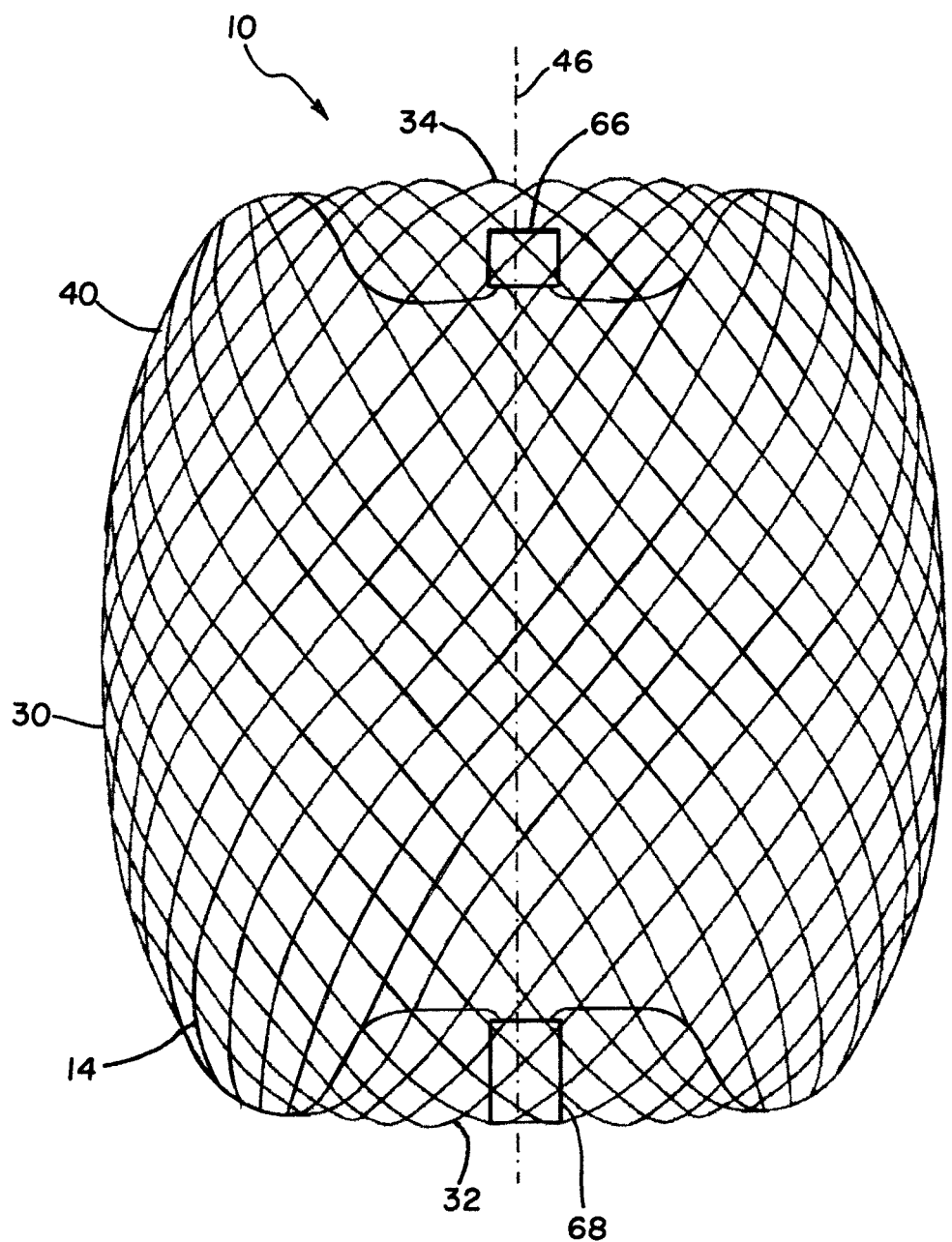
FIG. 2 is an elevation view of an embodiment of the implant device for treatment of a patient's vasculature shown in FIGS. 1A-1C.
Figure 22:
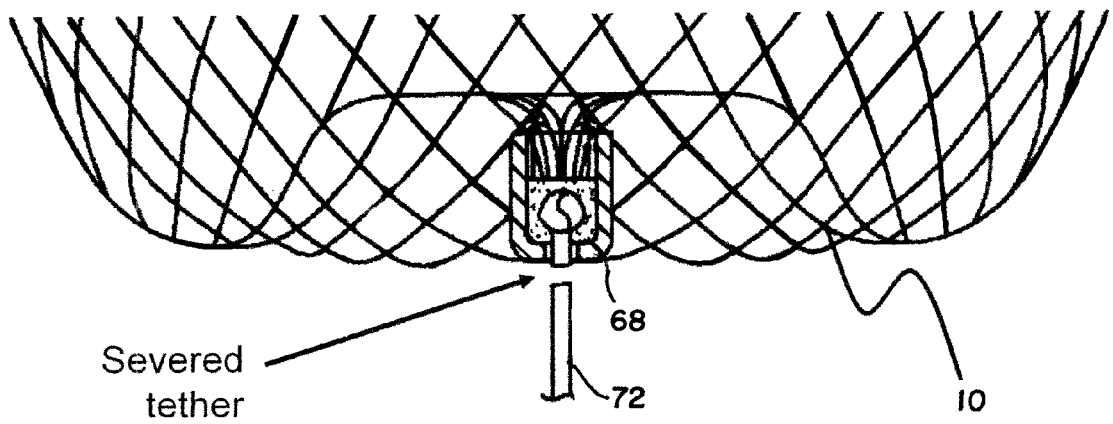
FIG. 22 is a partial elevation view of the implant device of FIG. 2, showing its detachment from the tether.

FIGS. 2 and 22 show an embodiment of an implant device 10 of FIGS. 1A-1C for treatment of a patient's vasculature. The implant device 10 may be in the form of a collapsible, open-celled lattice shell 30 that is formed from a meshwork of wires, fibers, threads, tubes or other filamentary elements 14 in one or more layers 40. The implant device 10 may be deployed and positioned intravascularly to treat a vascular defect. For some embodiments, the implant device 10 may have a globular shape that may be formed from such filaments by connecting or securing the ends of a tubular braided structure.

Figure 3:
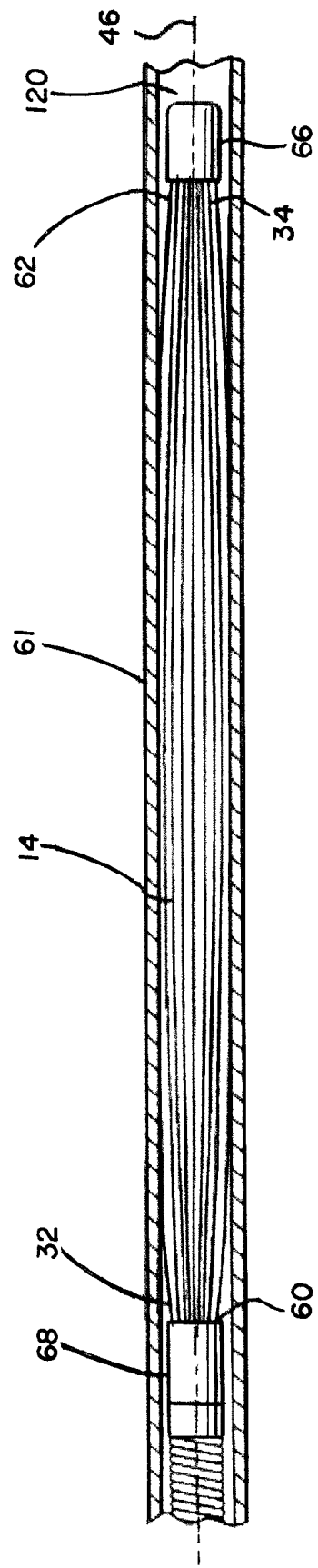
FIG. 3 is an elevation view in partial section of a distal end of the delivery apparatus of FIGS. 1A-1C with the implant device for treatment of a patient's vasculature disposed therein in a collapsed constrained state.

As such, once the implant device 10 is deployed, any blood flowing through the lattice of the shell 30 may be slowed to a velocity below the thrombotic threshold velocity, and thrombus will begin to form on and around the openings in the layers 40. Ultimately, this process may be configured to produce acute occlusion of the vascular defect within which the implant device 10 is deployed. The implant device 10 may have an everted filamentary structure with one or more layers 40, having a proximal end 32 and a distal end 34 in an expanded relaxed state. Each of the layers 40 has a substantially enclosed configuration for the embodiments shown. Some or all of the layers 40 of the implant device 10 may be configured to substantially block or impede fluid flow or pressure into a vascular defect or otherwise isolate the vascular defect over some period of time after the device is deployed in an expanded state. The implant device 10 generally also has a low profile, radially-constrained state, as shown in FIG. 3, with an axially-elongated tubular or cylindrical configuration that defines a longitudinal axis 46 between the proximal end 32 and the distal end 34. While in the radially-constrained state, the elongate flexible filamentary elements 14 of the layer or layers 40 may be disposed substantially parallel and in close lateral proximity to each other between the proximal end 32 and the distal end 34, forming a substantially tubular or compressed cylindrical configuration.

FIG. 3 shows an elevation view in partial section of a distal end of a delivery apparatus 112 with the implant device 10 while it is disposed in a microcatheter 61 in a collapsed, constrained state. The elongate flexible filamentary elements 14 of the layer or layers 40 of the implant device 10 may be disposed substantially parallel and in close lateral proximity to each other between the proximal end 32 and the distal end 34, forming a substantially tubular or compressed cylindrical configuration, as mentioned above. Proximal ends 60 of at least some of the filamentary elements 14 of the layer or layers 40 may be secured to a proximal hub 68, and distal ends 62 of at least some of the filamentary elements may be fixed to a distal hub 66, as shown in FIGS. 2 and 3. The proximal hub 68 and distal hub 66 are advantageously disposed substantially concentric to the longitudinal axis 46. A middle portion of the lattice shell 30 may have a first transverse dimension with a low profile suitable for delivery from the microcatheter 61. Radial constraint on the implant device 10 may be applied by an inside surface of the inner lumen of a microcatheter 61, such as the distal end portion of the microcatheter 61, or it may be applied by any other suitable mechanism that may be released in a controllable manner upon ejection of the implant device 10 from the distal end of the microcatheter 61. The proximal hub 68 of the implant device 10 is secured to the distal end of the delivery apparatus 112.

Figure 4:
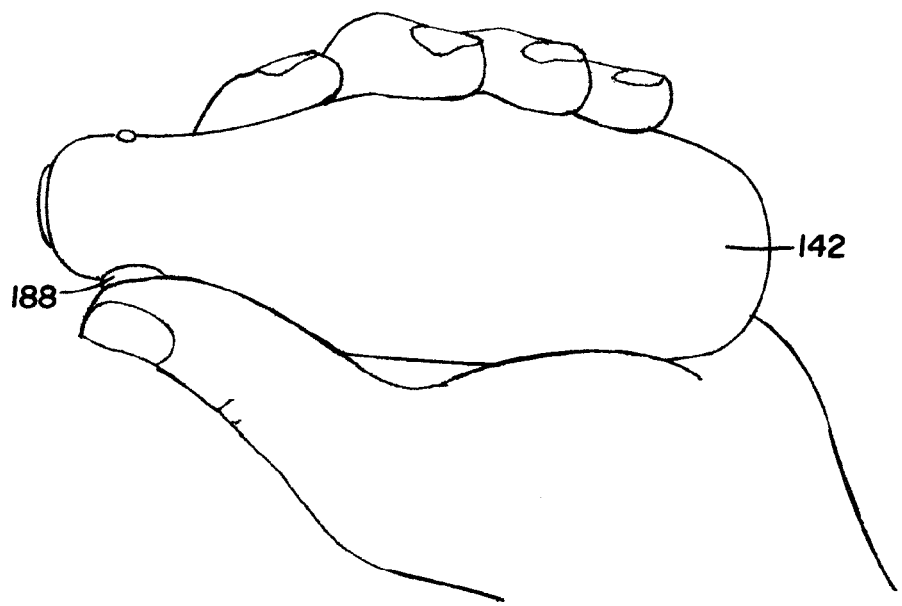
FIG. 4 is an elevation view of a hand-held controller for use in the system disclosed herein.
Figure 5:
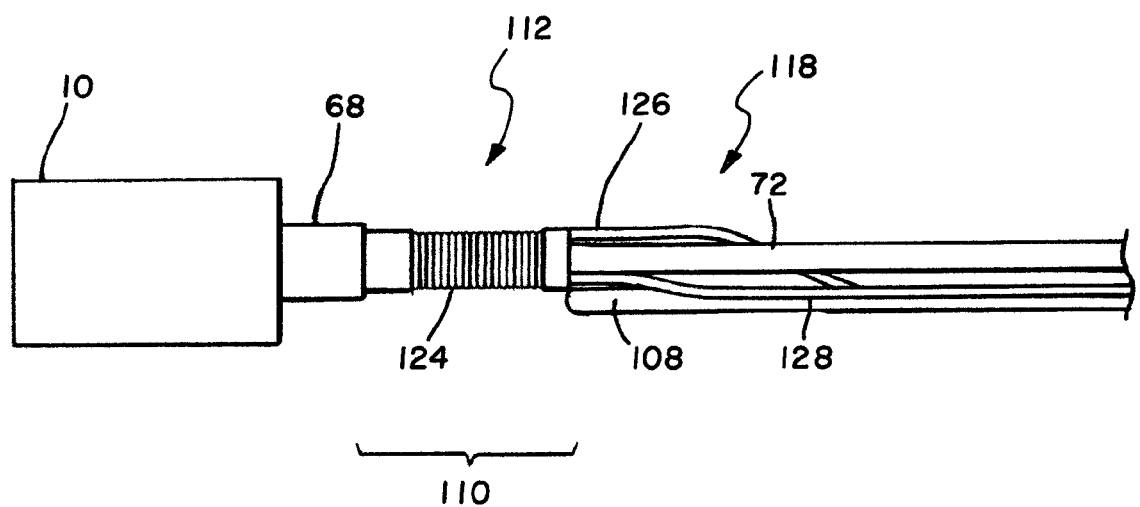
FIG. 5 is an elevation view of a distal portion of the delivery apparatus of FIGS. 1A-1C, showing internal structure thereof.
Figure 6:
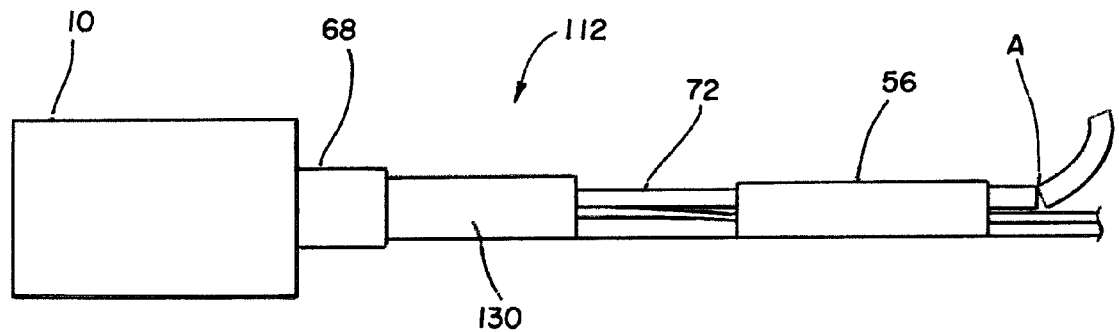
FIG. 6 is an elevation view of the distal portion of the delivery apparatus of FIGS. 1A-1C, with the addition of some tubular elements over the internal structures.

FIG. 4 illustrates use of a hand-held controller 142 that may house the electrical circuitry described herein, one or more batteries or other power source, contacts for engagement with the proximal end of the delivery apparatus 112, and a control switch 188 to close the circuit so that energy is delivered to a heating element (e.g. coil) 124, as described below.

Referring to FIGS. 5-8, an embodiment of the delivery apparatus 112 of the delivery system 100 of FIGS. 1A-1C is shown in more detail. The delivery apparatus 112 may include the elongated core wire 108 that may extend from a proximal end 76 of the delivery apparatus 112 to the distal section 118 of the delivery apparatus 112. The core wire 108 may be configured to provide sufficient column strength to push a constrained implant device 10 through an inner lumen 120 of the microcatheter 61 of the delivery system 100 as shown in FIGS. 1A-1C. The core wire 108 may also have sufficient tensile strength to withdraw or retract the implant device 10 from a position outside the microcatheter 61 and axially within the inner lumen 120 of the microcatheter 61. A tether 72 detachably connects the implant device to the delivery apparatus 112. The tether extends substantially linearly from the proximal hub 68 to the distal end of the core wire 108, in either a tensioned or a substantially non-tensioned state, with a substantially non-tensioned tether being preferred. The tether 72 may be secured to the distal end of the core wire 108 with a length of a second heat shrink tubing 56 that is disposed over a portion of the tether 72 and a distal section of the core wire 108 and shrunk over both. Alternatively, or in addition, a second adhesive 98 may be used as a suitable means of securing the tether 72 and the core wire 108 together as shown in FIG. 1C.

The heater coil 124, which is disposed coaxially around the distal portion of the tether 72, is coupled electrically to the first lead wire 126 and the second lead wire 128, as described below. The distal end of the coil 124 may advantageously be located proximally from the distal end of the tether 72 by a short distance. A length of a third heat shrink tubing 122 may be placed and shrunk over the heater coil 124, as shown in FIG. 1C. The third heat shrink tubing 122 may also be covered with a length of insulating tubing 130 (FIGS. 1C and 6), which may be a polyimide tubing. The insulating polyimide tubing 130 may serve as a heat shield, minimizing the leakage of heat from the heater coil 124 into the environment, such as the patient's blood stream. The third heat shrink tubing 122 and the insulating polyimide tubing 130 may bonded together with a third adhesive 74. Once the third heat shrink tubing 122 and the insulating polyimide tubing 130 have been secured, the proximal portion of the tether 72 disposed proximally of the second heat shrink tubing 56 may be trimmed as shown at the point A in FIG. 6.

Figure 7:
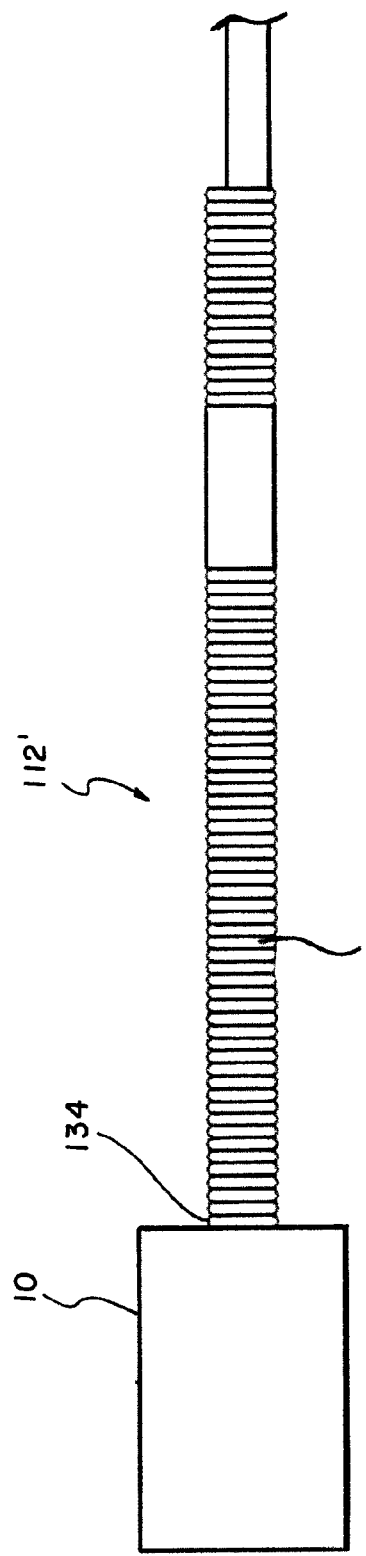
FIG. 7 is an elevation view of the distal portion of the delivery apparatus of FIGS. 1A-1C, with an over-coil in place.
Figure 8:
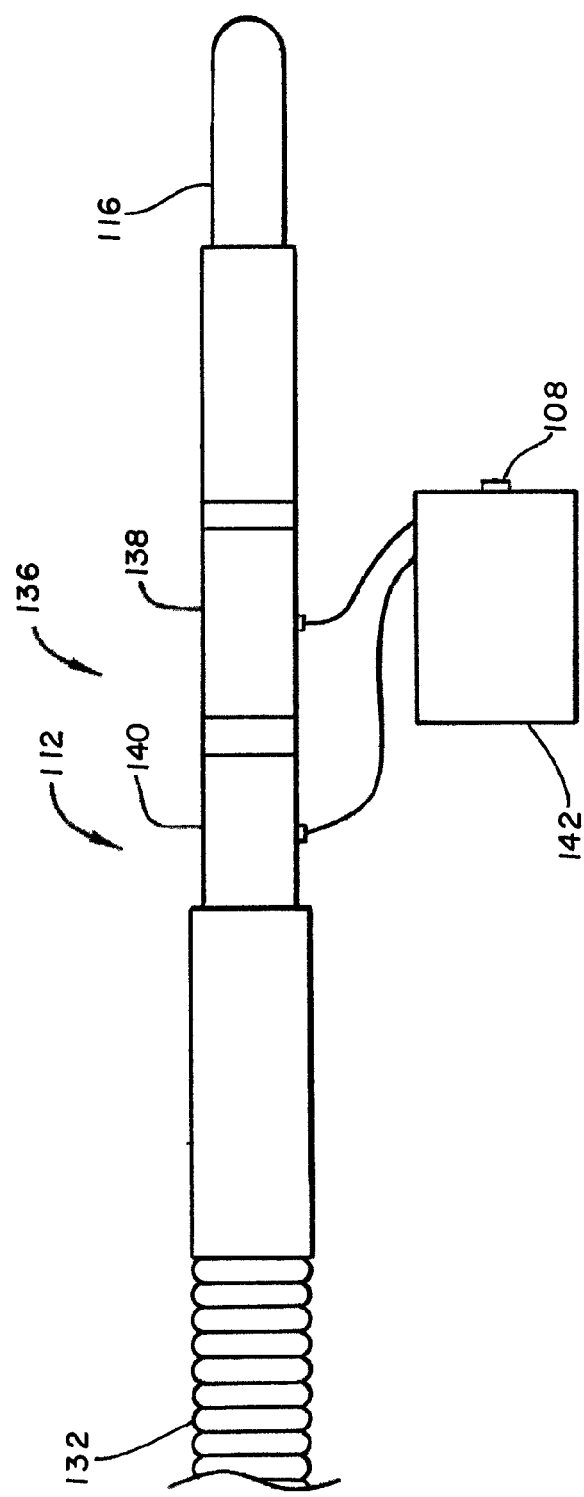
FIG. 8 is an elevation view of a proximal portion of the delivery apparatus of FIGS. 1A-1C.

As shown in FIGS. 7 and 8, the over-coil 132 that extends from the distal end 134 of the delivery apparatus 112 to the proximal section 136 of the delivery apparatus 112 may then be disposed over the heater coil 124, the core wire 108, the tether 72, the first lead wire 126 and the second lead wire 128 to hold these elements together, producing a low friction outer surface and maintaining the desired flexibility of the delivery apparatus 112. The proximal section 136 of the delivery apparatus 112 may include the proximal terminus of the over-coil 132, which may be disposed distally of a first contact 138 and a second contact 140, both of which may be circumferentially disposed about the proximal section of the core wire 108 and insulated therefrom. The first and second contacts 138, 140 are electrically coupled to the first lead wire 126 and the second lead wire 128, respectively, which are shown in FIG. 1A.

The first lead wire 126 has a first end connected to a first terminal 180 of the heater coil 124, and the second lead wire 128 has a first end connected to a second terminal 182 of the heater coil 124. See, e.g., FIG. 23. The first lead wire 126 has a second end connected to the first contact 138, and the second lead wire 128 has a second end connected to the second contact 140. The heater coil 124 receives electrical current supplied through the first lead wire 126 and the second lead wire 128 from an electrical power source (not shown) in the controller 142. The controller 142 is configured to engage the proximal section 136 of the delivery apparatus so as to couple the power source therein electrically to the first electric contact 138 and second electric contact 140, as shown in FIG. 8. The electrical current, preferably in the range of about 100 mA to about 200 mA, will then flow through the heater coil 124 so as to heat at least a portion of the heater coil (i.e., the heat-generating zone of the heater coil) to a temperature above the melting point of the tether material. When the tether 72 melts in the heat-generating zone of the heater coil, the tether 72 is severed, thereby detaching the implant device 10 from the delivery apparatus 112 for deployment in a target vascular site to which it has been delivered. In some cases a resistance value of the heater coil 124 may be in the range about 1.5 to 6 ohms, such as, for example, 4 to 6 ohms, and between about 15 mW and 240 mW electric power may be supplied to the heater coil 124 for about 1 second to melt the tether 72. In some embodiments, the controller 142 may supply either constant current or constant voltage to the heating element.

Embodiments of the delivery apparatus 112 may generally have a length greater than the overall length of the microcatheter 61 to be used for the delivery apparatus 112. This relationship may allow the delivery apparatus 112 to extend, along with the implant device 10 secured to the distal end thereof, from the distal port of the inner lumen 120 of the microcatheter 61, while having sufficient length extending from a proximal end 150 of the microcatheter 61, shown in FIG. 16 and discussed below, to enable manipulation thereof by a physician. For some embodiments, the length of the delivery apparatus 112 may be in the range about 170 cm to about 200 cm. The core wire 108 may be made from any suitable high strength material such as stainless steel, NiTi alloy, or the like. Embodiments of the core wire 108 may have an outer diameter or transverse dimension of about 0. 0.25 mm to about 0.38 mm. The over-coil 132 may have an outer diameter or transverse dimension of about 0.46 mm to about 0.76 mm.

Although the delivery apparatus embodiment 112 shown in FIGS. 5-8 is activated by electrical energy passed through a conductor pair, a similar configuration may be employed that utilizes light energy passed through a fiber optic or any other suitable arrangement may be used to remotely heat a distal heating member or element such as the heater coil 124 to sever the distal portion of the tether 72. In addition, other delivery apparatus embodiments are discussed and incorporated herein that may also be used for any of the medical device embodiments for treatment of a patient's vasculature discussed herein.

In another embodiment, shown in FIGS. 23 and 23A, the heating element or heater coil may comprise a plurality of zones where the coil has a different pitch. (The pitch of a coil is the width of one complete coil turn, measured along the coil axis.) A small or tight pitch (e.g., a pitch of between about 0.018 mm and about 0.38 mm) may be useful for the attachment of lead wires and for isolating the heating zone to create a small, focused heating zone, and thus a sharp and narrow severing of the tether. A large or open pitch (e.g., of between about 0.38 mm and about 0.76 mm) may be useful for creating a zone of minimal heating zone and for isolating lead wire attachment zones from the heating zone.

In this embodiment, a heater coil 124' is wound around the tether 72 in four winding zones: a first (proximal) winding zone Z1 with a small or tight pitch, a second winding zone Z2 located distally from the first winding zone Z1, with a large or open pitch, a third or distal winding zone Z3 with a small or tight pitch and a fourth winding zone Z4 with a tight pitch. In the third winding zone Z3, the coil winding may advantageously be doubled back or reversed upon itself, as shown in FIG. 23A, to form a double winding region encompassing the third winding zone Z3 and a portion Z2' of the second winding zone Z2 between the third winding zone Z3 and the fourth winding zone Z4. In this double winding region, the coil 124' has, effectively, two winding layers. Thus, as shown in FIG. 23, the second winding zone Z2 has a first portion with a single winding layer and a second portion Z2' with a double winding layer, wherein the fourth winding zone Z4 is located between the first and second portions of the second winding zone Z2.

An insulating tube 150, preferably of a thermally-insulative polymer such as polyimide, is placed coaxially around the coil 124' from a point distal from the third winding zone Z3 to a point proximal from the fourth winding zone Z4. The insulating tube 150 is covered with a shrink-wrap tubing 152, which extends proximally past the first winding zone Z1.

The first lead wire 126 is connected to the heating element 124' at the first terminal 180 in the first winding zone Z1. The second winding zone Z2 may provide a low resistance portion of the coil 124'. In some embodiments, the distal-most winding zone Z3 is the primary heat-generating zone that generates sufficient heat to melt the tether 72, thereby severing the tether 72 in a narrow cut, as described herein. The doubling of the winding in the third winding zone Z3 may enhance the ability of the coil 124' to generate sufficient heat in this zone to achieve a tether melting temperature within a very narrow space, e.g. 0.1 to 0.5 mm, with as few as 2 to 10 windings, (for example, between 2 and 5 windings) depending on the gauge of the wire, the material of the wire, and the current applied to the coil 124'. This narrow heat-generating zone facilitates a sharp severing of the tether 72. This heat generating zone (i.e., the third winding zone Z3) is advantageously disposed a short distance proximally from the distal end of the tether 72, so that detachment of the implant device 10 from the pusher apparatus 112 by the severance of the tether 72 occurs close to the proximal end of the implant device 10.

At a point B near the proximal end of the double winding region and distally from the fourth winding zone Z4, one wire of the coil may exit from the insulating tube 150 so as to be wound over the insulating tube 150 to form the fourth winding region Z4, as shown in FIG. 23. The second lead wire 128 is connected to second terminal 182 of the heater coil 124' in the fourth winding zone Z4.

Figure 24B:
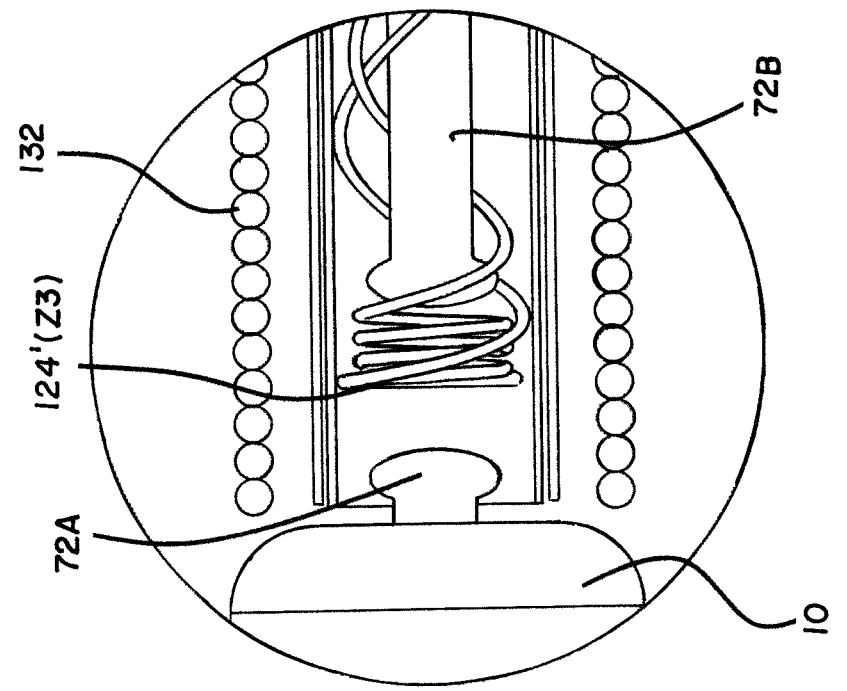
FIGS. 24A and 24B are detailed views of the distal portion of the heater coil, showing the process of thermally severing the tether connected the implant device to the delivery apparatus.
Figure 24A:
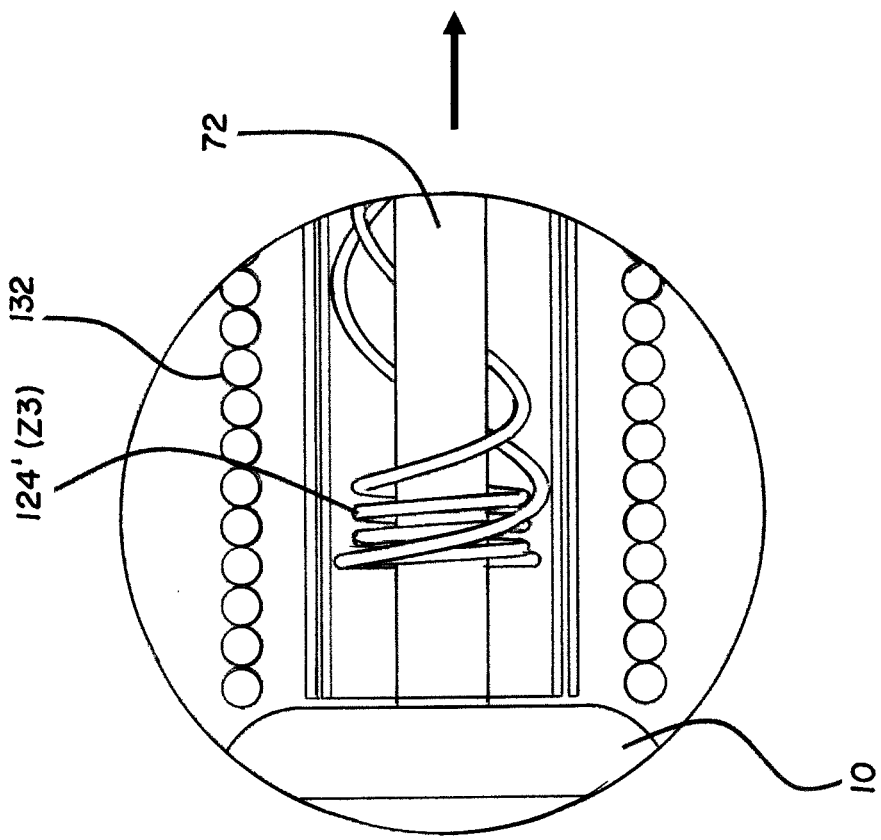

FIGS. 24A and 24B show the tether 72 being severed by the heat generated in the third winding zone Z3 of the heater coil 124'. The end 72A of the tether 72 that is attached to the implant device 10 may be just distally beyond the distal end of the heater coil 124'. The end 72B of the tether 72 that remains attached to the core wire 108 may be inside the heater coil 124'.

Device embodiments discussed herein may be releasable from any suitable flexible, elongate delivery apparatus or actuator, such as a guidewire or guidewire-like structure. The release of device embodiments from such a delivery apparatus may be activated by a thermal mechanism, as discussed above, an electrolytic mechanism, a hydraulic mechanism, a shape memory material mechanism, or any other mechanism known in the art of endovascular implant deployment.

Embodiments for deployment and release of medical implant devices, such as deployment of embolic devices or stents within the vasculature of a patient, may include connecting such a device via a releasable connection to a distal portion of a pusher or other delivery apparatus member. The implant device 10 may be detachably mounted to the distal portion of the delivery apparatus 112 by a filamentary tether, string, thread, wire, suture, fiber, or the like, any of which may serve as the tether 72. The tether 72 may be in the form of a monofilament, rod, ribbon, hollow tube, or the like. Some embodiments of the tether 72 may have a diameter or maximum thickness of between about 0.05 mm and 0.2 mm. In some cases, the tether 72 may be configured to be able to withstand a maximum tensile load having a mass of between about 0.5 kg and 5 kg. For some embodiments, due to the mass of a medical device being deployed that may be substantially greater than other medical devices, it may be desirable to use high strength fibers for tether embodiments that may have a "load at break" greater than about 15 Newtons.

For some embodiments, a tether made from a material known as Dyneema Purity, available from Royal DSM, Heerlen, Netherlands, may be used.

The tether 72 may be severed by the input of energy such as electric current to a heating element causing release of the therapeutic device. For some embodiments, the heating element may be a coil of wire with high electrical resistivity such as a platinum-tungsten alloy. The tether 72 may pass through or be positioned adjacent the heater element. The heater may be contained substantially within the distal portion of the delivery apparatus 112 to provide thermal insulation, reducing the potential for thermal damage to the surrounding tissues during detachment. In another embodiment, current may pass through the tether, which would thus also act as a heating element.

Many materials may be used to make the tether 72, including polymers, metals, and composites thereof. One class of materials that may be useful for tethers includes polymers such as polyolefin, polyolefin elastomer, polyethylene, polyester (PET), polyamide (Nylon), polyurethane, polypropylene, block copolymers such as PEBAX or the thermoplastic polyester elastomer marketed by E. I. DuPont de Nemours under the trademark Hytrel®, ethylene vinyl alcohol (EVA), or rubbery materials such as silicone, latex, and similar flexible polymers such as those produced by Kraton Polymers U.S., LLC, of Houston, Tex. A particularly useful material for the tether is Paramyd®, which is a para-aramid (poly-par-aphenyleneterepthalamide) and is commercially available from Aramid, Ltd., Hilton Head, S.C. In some cases, the polymer may also be cross-linked by radiation to manipulate its tensile strength and melt temperature. Another class of materials that may be used for tether embodiments may include metals such as nickel titanium alloy (Nitinol), gold, platinum, tantalum, and steel. Other materials that may be useful for tether construction include wholly aromatic polyester polymers which are liquid crystal polymers (LCP) that may provide high performance properties and are highly inert. A commercially available LCP polymer is Vectran, which is produced by Kuraray Co. (Tokyo, Japan). The selection of the material may depend on the melting or softening temperature, the power used for detachment, and the body treatment site. The tether may be joined to the implant and/or the core wire 108 by crimping, welding, knot tying, soldering, adhesive bonding, or other means known in the art.

Referring to FIGS. 9-13, partial cross-sectional views of different embodiments of a detachment device 110, including the heater coil 124 are shown. The detachment device 110 may be adapted to sever the tether 72, in order to detach the implant device 10 from the delivery apparatus 112. The detachment device 110 may be configured to prevent fluid 148, for example, saline and/or blood, to seep into a detachment chamber 146 defined in a space between the heater coil 124 and the tether 72, since presence of fluid 148 would absorb part of the heat, thereby making a tether melting process less reliable. The detachment device 110 may also be configured to avert a melted tether fusing to the heater coil 124, thereby preventing the deployment of the implant device 10.

A length of the third heat shrink tubing 122 may be shrunk over the heater coil 124. The third heat shrink tubing 122 may be covered with a length of insulating polyimide tubing 130. The axially placed tether 72 may be centered within the detachment chamber 146. As described above, the implant device 10 may be detached from the delivery apparatus 112 by melting the tether 72 inside the detachment device 110. The tether 72 may be melted by the heat generated by the heater coil 124. To reliably sever the tether 72, the detachment chamber 146 may be protected from fluid seepage by a fluid shielding member, as discussed below. A dry, fluid-free detachment chamber 146 may assure a controlled, predictable tether melting process.

Figure 9:
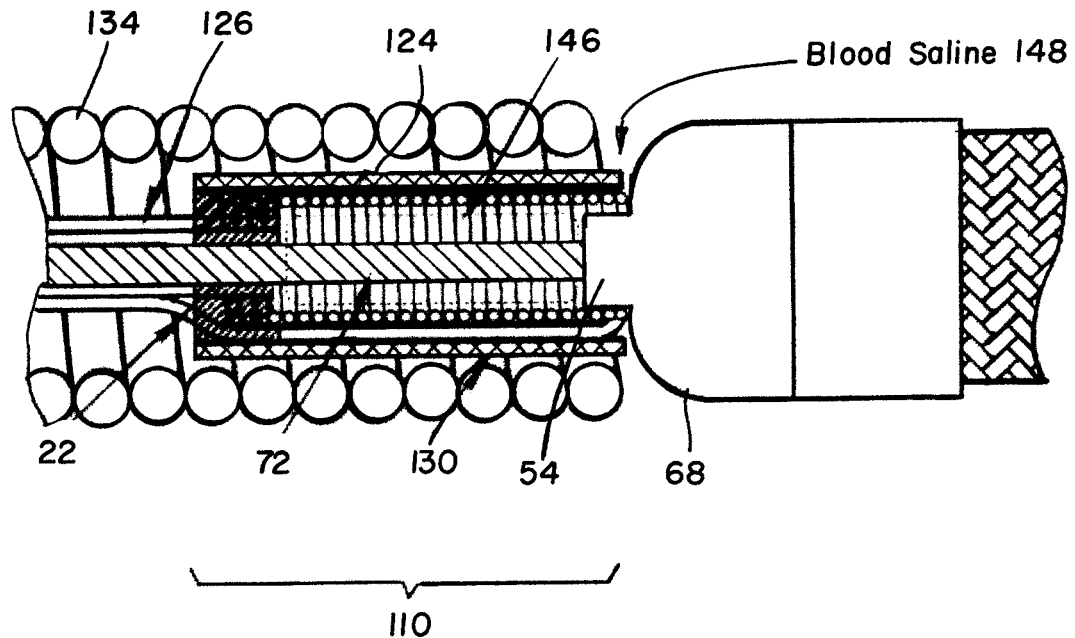
FIGS. 9-13 are partial cross-sectional views of different embodiments of a detachment device of the delivery apparatus of FIGS. 1A-1C.

FIG. 9 illustrates an embodiment of the detachment device 110 including a neck portion 52 that may be formed at a proximal end of the proximal hub 68 to serve as the fluid shielding member. The neck portion 52 of the proximal hub 68 may extend into the distal end of the detachment device 110, thereby preventing seepage of the fluid 148 into the detachment chamber 146.

Figure 10:
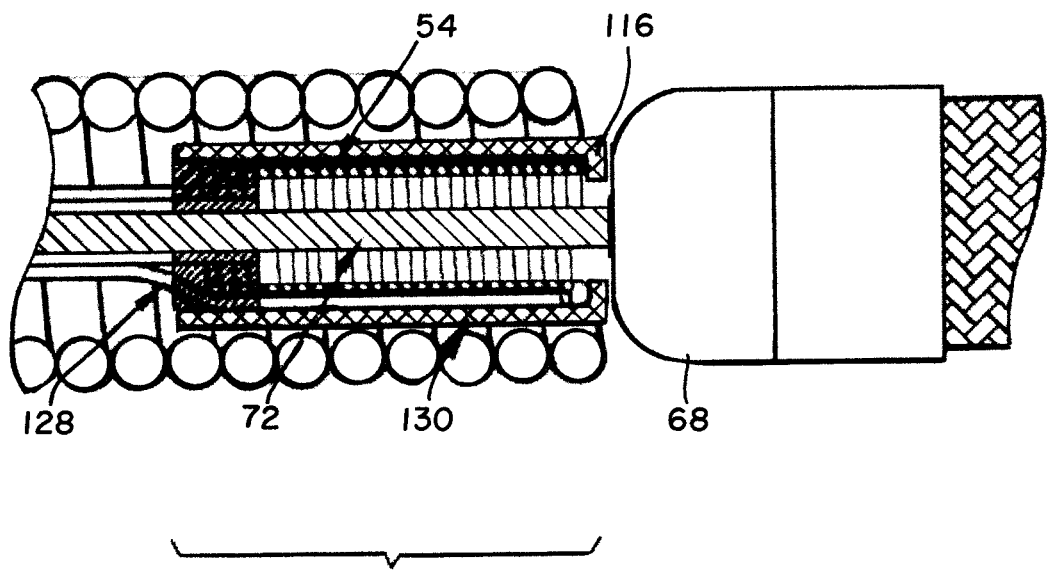

FIG. 10 illustrates an embodiment of the detachment device 110, including a circumferential lip or rim 116 that may be formed at the distal end of the insulating polyimide tubing 130. The rim 116 may work as the fluid shielding member and may effectively seal the detachment chamber 146 from penetration of the fluid 148.

Figure 11:
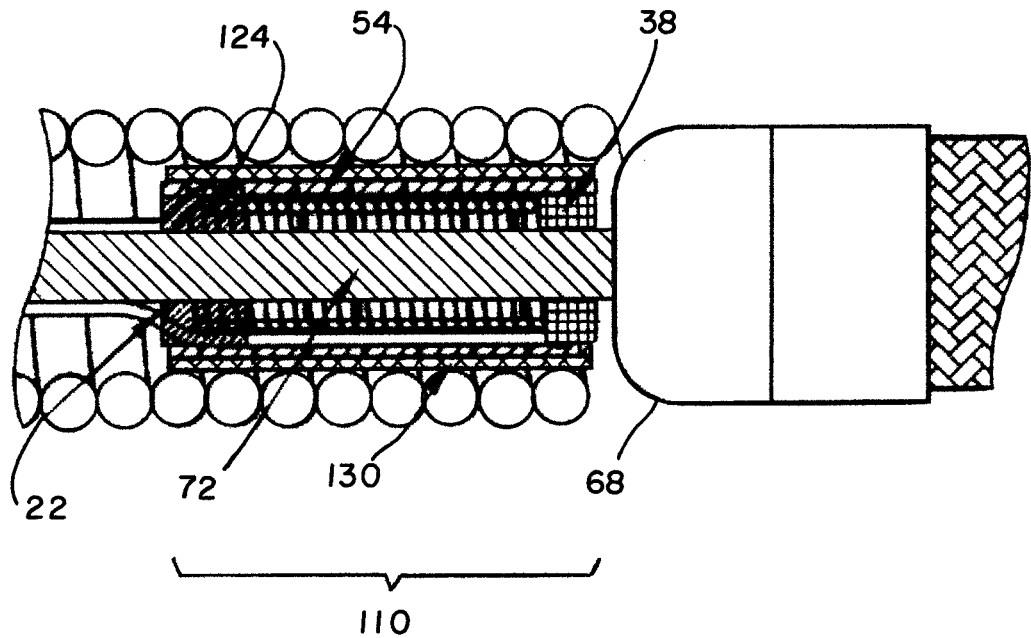
Figure 12:
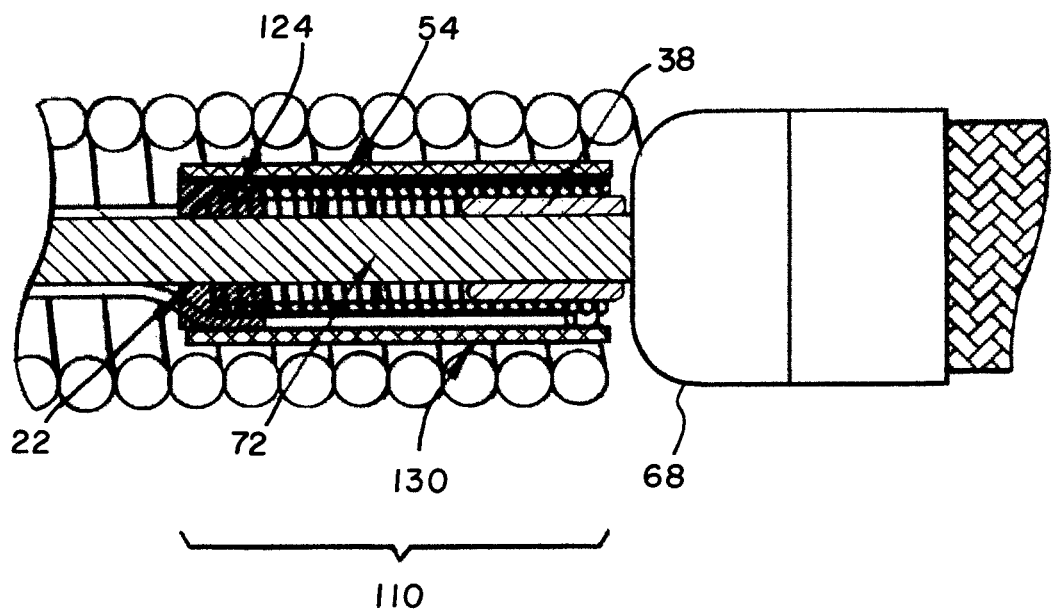

FIGS. 11-12 illustrate an embodiment of the detachment device 110, including a soft O-ring 38 (FIG. 11) or a hydrogel sealant 58 (FIG. 12), which may be disposed between the insulating polyimide tubing 130 and the tether 72 at the distal end of the detachment device 110. The soft O-ring 38 or the hydrogel sealant 58 may work as the fluid shielding members.

Figure 13:
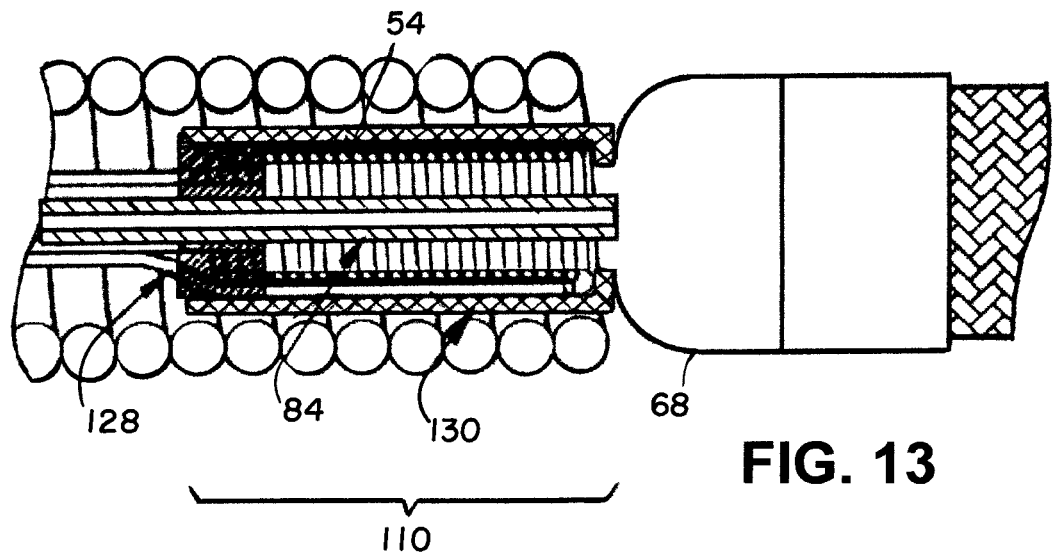

FIG. 13 illustrates an embodiment of the detachment device 110 that is similar to the previously described embodiments, except that in this embodiment of the detachment device 110, a tubular tether 84 is used instead of the solid tether 72. The use of the tubular tether 84 may offer some advantages over the use of the solid tether 72. For instance, it may take less energy to sever the tubular tether 84 than it does to sever the solid tether 72.

Figure 14:
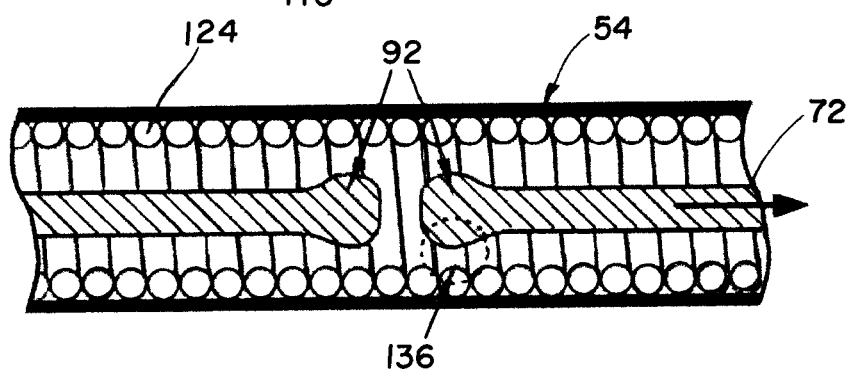
FIGS. 14-15 are views in cross-section of melted tethers in different detachment device embodiments.
Figure 15:
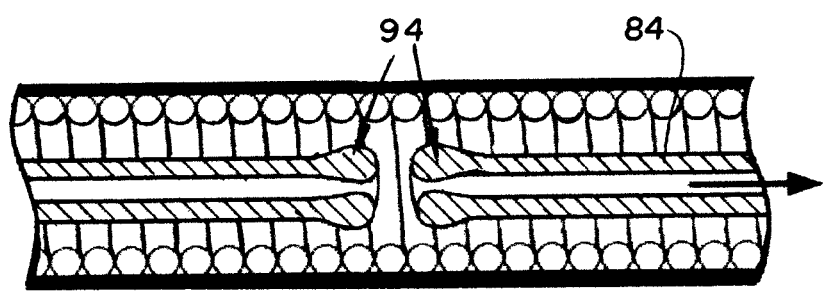

FIGS. 14-15 show cross-sectional views of embodiments of the tethers 72 and 84 after thermally-induced separation. As discussed above, in order to sever a tether, a segment of the tether's material may be melted. Surface tensions of the melted terminal portion of the tethers 72 and 84 may form termination balls or globs 92 (FIG. 14) and 94 (FIG. 15) on the respective terminal portion of the tethers 72, 84, respectively. In some general cases the termination ball 92 formed on the solid tether 72 may be larger than the termination ball 94 formed on the tubular tether 84 with similar outside dimensions. In some extreme cases a large termination ball may fuse to the heater coil 124 (at site 136) preventing a successful detachment of the implant device 10. In order to prevent the formation of large termination balls, the outside dimensions of the solid tether 72 may be chosen to be smaller than the outside dimensions of the tubular tether 84. It is noted that a tubular tether 84 may form smaller termination balls 94 upon being severed, as compared to the termination balls 92 that may be formed on a solid tether 72, may be a result of the wicking of some of the melted material into the hollow interior of the tubular tether 84 after it is severed.

Figure 16:
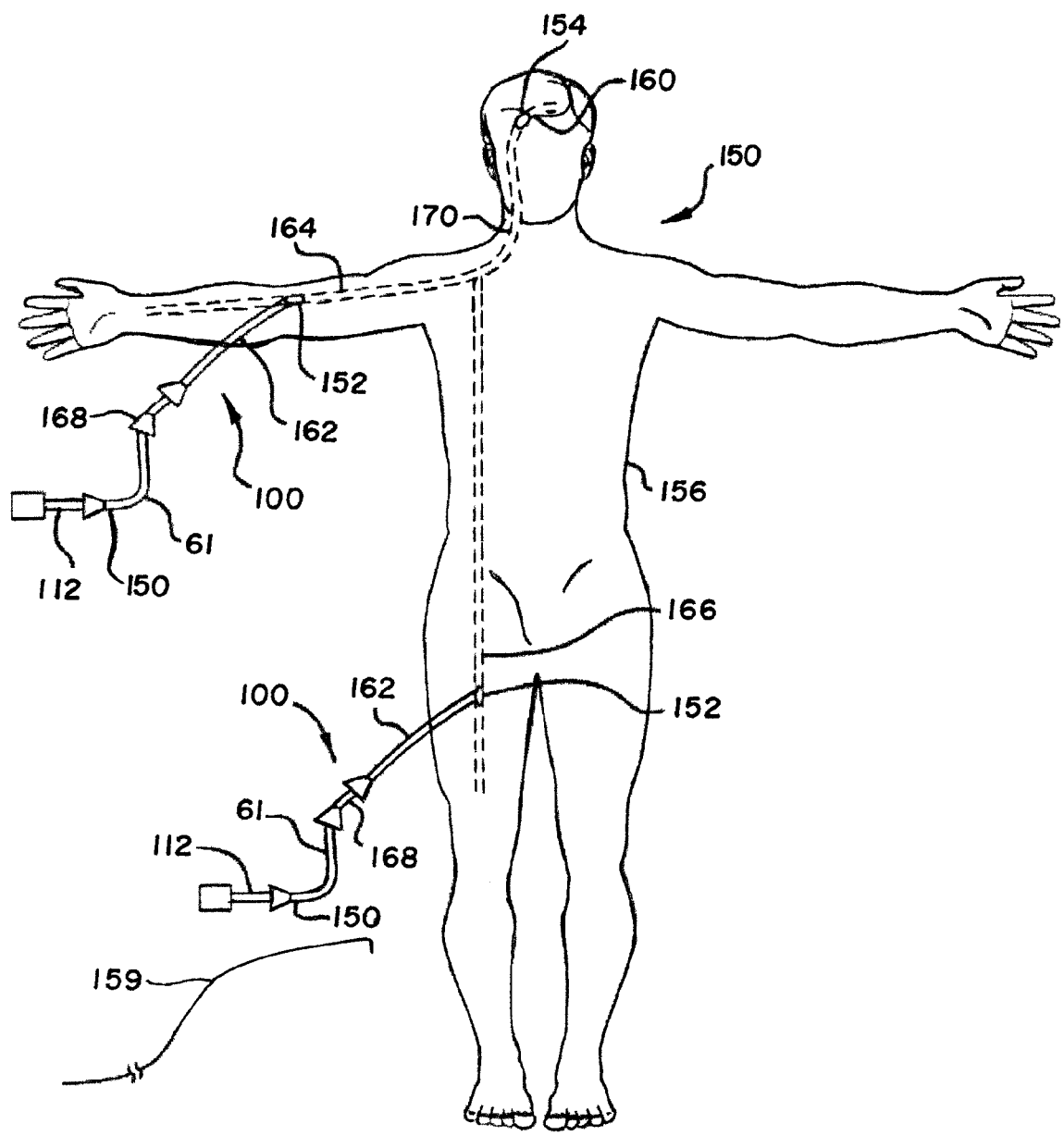
FIG. 16 is a schematic view of a patient being accessed by an introducer sheath, a microcatheter, and the implant device detachably connected to a distal end of the delivery apparatus for treatment of vasculature.

FIG. 16 illustrates a schematic view of a patient 158 undergoing treatment of a vascular defect 160. The implant device 10 discussed herein may be delivered and deployed by the delivery system 100 that may include a microcatheter 61, that is known in the art of neurovascular navigation and therapy. The implant device 10 may be elastically collapsed and restrained by a tube or other radial restraint, such as an inner lumen 120 of the microcatheter 61, for delivery and deployment. The microcatheter 61 may generally be inserted through a small incision 152 accessing a peripheral blood vessel, such as the femoral artery or brachial artery. The microcatheter 61 may be delivered or otherwise navigated to a desired treatment site 154 from a position outside the patient's body 156 over a guidewire 159 under fluoroscopy or by other suitable guiding methods. The guidewire 159 may be removed during such a procedure to allow insertion of the implant device 10 secured to the delivery apparatus 112 of the delivery system 100 through the inner lumen 120 of the microcatheter 61.

An access sheath 162 is shown disposed within either a radial artery 164 or femoral artery 166 of the patient 158 with a delivery system 100 that includes the microcatheter 61 and delivery apparatus 112 disposed within the access sheath 162. The delivery apparatus 112 is shown extending distally into the vasculature of the patient's brain adjacent a vascular defect 160 in the patient's brain.

Access to a variety of blood vessels of a patient may be established, including arteries such as the femoral artery 166, the radial artery 164, and the like, in order to achieve percutaneous access to a vascular defect 160. In general, the patient 158 may be prepared for surgery, the access artery is exposed via a small surgical incision 152, and access to the lumen is gained using the Seldinger technique where an introducing needle is used to place a wire over which a dilator or series of dilators may dilate a vessel allowing an access sheath 162 to be inserted into the vessel. This would allow the device to be used percutaneously. With an access sheath 162 in place, a guiding catheter 168 is used to provide a safe passageway from the entry site to a region near a treatment site 154. For example, in treating a site in the human brain, a guiding catheter 168 would be chosen which would extend from the small surgical incision 152 at the femoral artery up through the large arteries extending around the heart through the aortic arch, and downstream through one of the arteries, extending from the upper side of the aorta such as the carotid artery 170. Typically, a guidewire 159 and a neurovascular microcatheter 61 are then placed through the guiding catheter 168 and advanced through the patient's vasculature, until a distal end 151 of the microcatheter 61 is disposed adjacent or within the target vascular defect 160, such as an aneurysm. Exemplary guidewires 159 for neurovascular use may include the Synchro2® made by Boston Scientific and the Glidewire Gold Neuro® made by MicroVention Terumo. Typical guidewire sizes may include 0.014 inches (0.36 mm) and 0.018 inches (0.46 mm). Once the distal end 151 of the microcatheter 61 is positioned at the site, often by locating its distal end through the use of radiopaque marker material and fluoroscopy, the catheter is cleared. For example, if a guidewire 159 has been used to position the microcatheter 61, it may be withdrawn from the microcatheter 61, and then the delivery apparatus 112 may be advanced through the microcatheter 61.

FIGS. 17-19 show a deployment sequence of the implant device of FIG. 2 for treatment of a patient's vasculature. Delivery and deployment of the implant device 10 discussed herein may be carried out by first compressing the implant device 10, or any other suitable implantable medical device for treatment of a patient's vasculature as discussed above. While disposed within the microcatheter 61 or other suitable delivery device, as shown in FIG. 3, the filamentary elements 14 of the layers 40 may take on an elongated, non-everted configuration substantially parallel to each other and to a longitudinal axis of the microcatheter 61. Once the implant device 10 is pushed out of the distal port of the microcatheter 61, or the radial constraint is otherwise removed, the distal ends 62 of the filamentary elements 14 may then axially contract towards each other, so as to assume the globular everted configuration within the vascular defect 160 as shown in FIG. 18. The implant device 10 may then be delivered to a desired treatment site 154 while disposed within the microcatheter 61, and then ejected or otherwise deployed from a distal end 151 of the microcatheter 61. In other method embodiments, the microcatheter 61 may first be navigated to a desired treatment site 154 over a guidewire 159 or by other suitable navigation techniques. The distal end of the microcatheter 61 may be positioned such that a distal port of the microcatheter 61 is directed towards or disposed within a vascular defect 160 to be treated and the guidewire 159 withdrawn. The implant device 10 secured to the delivery apparatus 112 may then be radially constrained, inserted into a proximal portion of the inner lumen 120 of the microcatheter 61, and distally advanced to the vascular defect 160 through the inner lumen 120. Once the distal tip or deployment port of the delivery system 100 is positioned in a desirable location adjacent or within a vascular defect 160, the implant device 10 may be deployed out of the distal end of the microcatheter 61, thus allowing the device to begin to radially expand as shown in FIG. 19. As the implant device 10 emerges from the distal end of the delivery apparatus 112, the implant device 10 may start to expand to an expanded state within the vascular defect 160, but may be at least partially constrained by an interior surface of the vascular defect 160.

Figure 20:
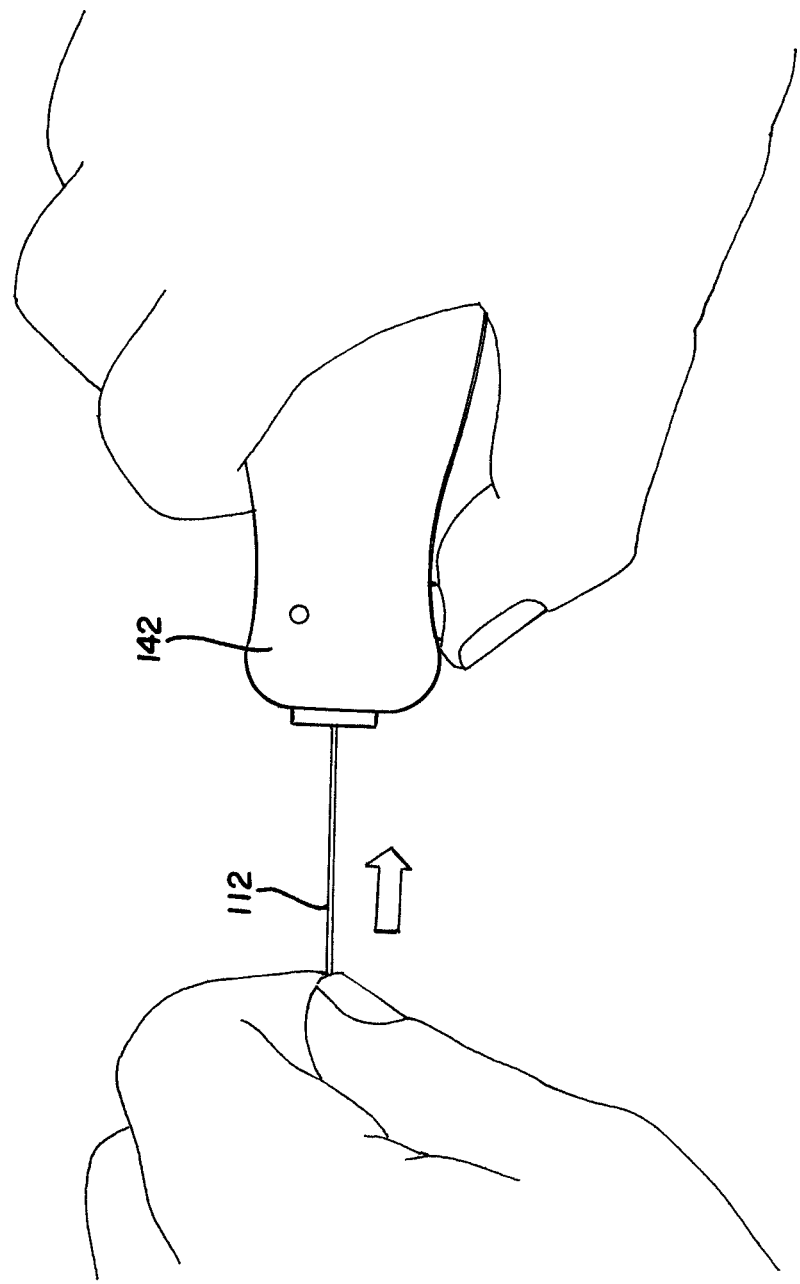
FIG. 20 is an elevation view of the hand-held controller of FIG. 4, with the proximal end of the delivery system engaged for connection of the electrical system.

At this time the implant device 10 may be detached from the delivery apparatus 112. The detachment may be brought about by the application of energy to the heater coil 124 from an electrical energy source. The electrical energy source may be housed in a hand-held controller 142 as described above and as shown in FIG. 4. The proximal end of the delivery apparatus 112 may be inserted into a receptacle in the controller 142, as shown in FIG. 20. Electrical contacts on the proximal end of the delivery apparatus (such as the contacts 138 and 140 shown in FIG. 8) are aligned with contacts (not shown) inside the controller 142. The implant device detachment may be initiated by turning-on a momentary control switch 188 (FIG. 4) disposed on the controller 142. The momentary control switch 188 may couple the electrical energy source (not shown) in the controller 142, for example a battery, to the heater coil 124 via a pair of conductors, such as the first lead wire and 126 and the second lead wire 128 shown in FIG. 1A and described above.

For efficient use of the energy source in the controller 142, it may be preferable to assure that the resistance of the first and second lead wires 126 and 128 is less than the resistance of the heater coil 124. A single activation of the momentary control switch 188 may allow current flow to the heater coil 124 for aduration of about 1 second. In some embodiments, the duration of the current flow may be between about 180 and 2000 milliseconds. During this current flow, thermal energy, in a range of about 350 to 550 millijoules, may be dissipated by the heater coil 124. In some embodiments, the heat generated from the heater coil for 1 second may be sufficient to melt and sever the tether 72, 84 that secures the proximal hub 68 of the implant device 10 to the delivery apparatus 112. A separate hand-held controller 142, as shown in FIG. 4, may be utilized to house the energy source, the control circuitry (not shown), and the control switch 188, and electrical terminals (not shown) that make electrical make electrical contact with the contacts 138, 140 on the proximal section 136 of the delivery apparatus 112.

Figure 21:
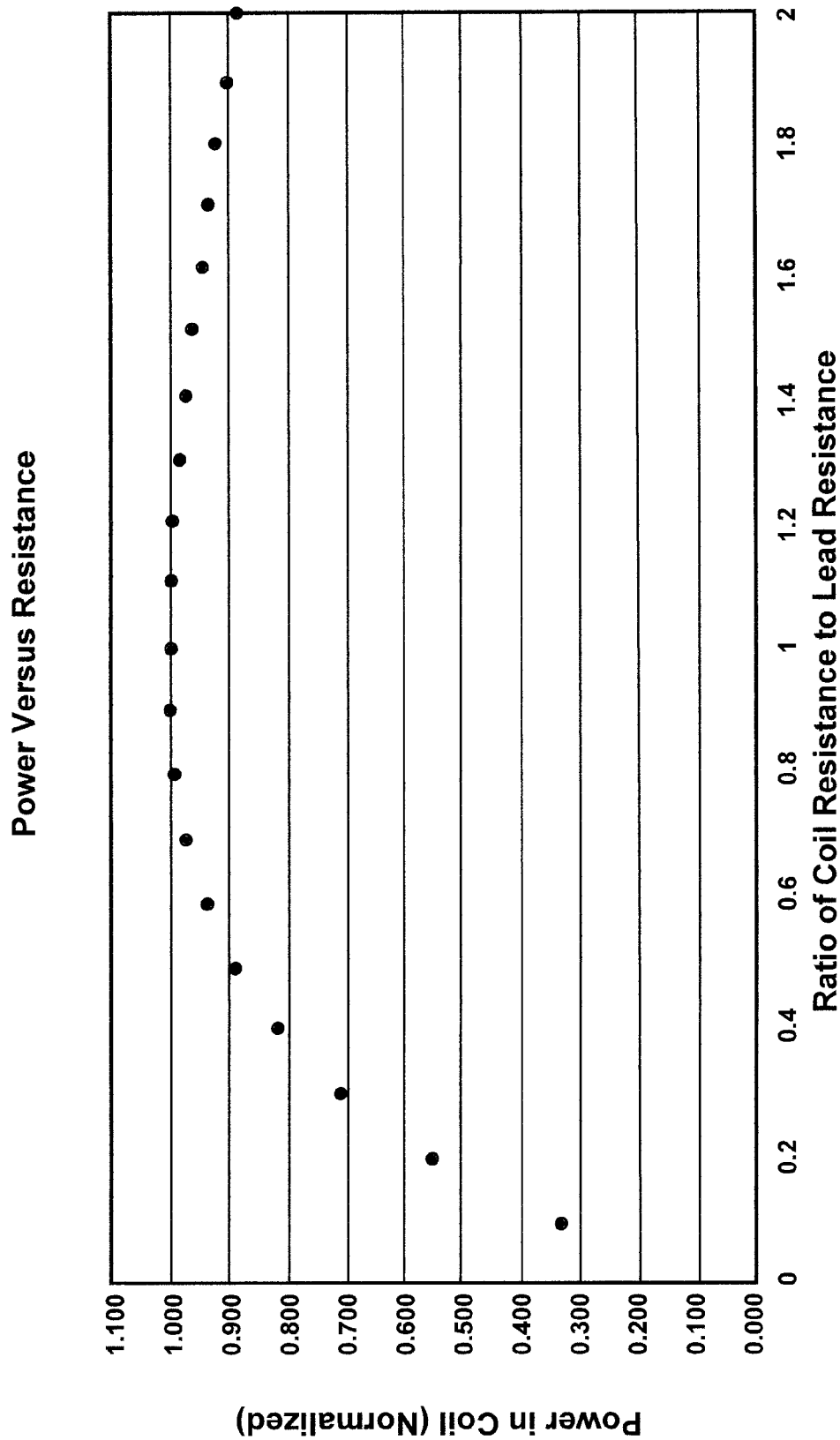
FIG. 21 is a graph showing heating coil power as a function of the ratio of heating coil resistance to lead wire resistance.

The power transferred to the coil 124 is maximized when the heater coil resistance equals the resistance of the lead wires 126, 128 that connect the heater coil 124 to the contacts 138, 140, respectively. This is known as "impedance matching." FIG. 21 shows this relationship: The electrical power falls off steeply to the left side of "1" on the x axis—which is the ratio of the heater coil resistance and lead wire resistance. Conversely, the electrical power falls off shallowly as the ratio of resistances moves to the right of "1". In some embodiments, the heater coil resistance may be equal to or somewhat higher than the lead wire resistances. In some embodiments ratio of the heater coil resistance to lead wire resistance may be between about 0.6 and 1.6, such as, for example, between about 0.9 and 1.4.

Upon full deployment, radial expansion of the implant device 10 may serve to secure the implant device 10 within a vascular defect 160 and also to deploy the implant device 10 across at least a portion of an opening 190 (e.g., aneurysm neck) in the vascular defect, so as to at least partially isolate the vascular defect 160 from flow, pressure, or both of the patient's vasculature adjacent the vascular defect 160, as shown in FIG. 16.

Once the implant device 10 is deployed at a desired treatment site 154, the microcatheter 61 may then be withdrawn. Characteristics of the implant device 10 and delivery apparatus 112 discussed herein generally allow for retraction of the implant device 10 after initial deployment into the vascular defect 160, but before detachment of the implant device 10. Therefore, it may also be possible and desirable to withdraw or retrieve an initially deployed implant device 10 after the fit within the vascular defect 160 has been evaluated in favor of a differently-sized implant device 10. The tip 151 of a catheter, such as the microcatheter 61, may be advanced into or adjacent to the vascular site or vascular defect 160 (e.g. aneurysm) as shown in FIG. 17. An example of a suitable microcatheter 61 having an inner lumen diameter of about 0.51 mm to about 0.56 mm is the Rapid Transit® manufactured by Cordis Corporation. Examples of some suitable microcatheters 61 may include microcatheters having an inner lumen diameter of about 0.66 mm to about 0.71 mm, such as the Rebar® by Ev3 Company, the Renegade Hi-Flow® by Boston Scientific Corporation, and the Mass Transit® by Cordis Corporation. Suitable microcatheters having an inner lumen diameter of about 0.79 mm to about 0.84 mm may include the Marksmen® by Chestnut Medical Technologies, Inc. and the Vasco 28® by Balt Extrusion. A suitable microcatheter 61 having an inner lumen diameter of about 1.0 mm to about 1.04 mm includes the Vasco 35® by Balt Extrusion. These microcatheters 61 are listed as exemplary embodiments only, and other suitable microcatheters may also be used with any of the embodiments discussed herein.

For some embodiments, as discussed above, the implant device 10 may be manipulated by the user to position the implant device 10 within the vascular treatment site 154 or in the vascular defect 160 during or after deployment but prior to detachment. For some embodiments, the implant device 10 may be rotated in order to achieve a desired position of the implant device 10 and, more specifically, a desired position of the layer or layers 40, prior to or during deployment of the implant device 10. For some embodiments, the implant device 10 may be rotated about a longitudinal axis of the delivery system 100 with or without the transmission or manifestation of torque being exhibited along a middle portion of a delivery catheter. These delivery and deployment methods may be used for deployment within berry aneurysms, terminal aneurysms, or any other suitable vascular defect embodiments.

Any embodiment of the implant device 10 or the delivery apparatus 112 discussed herein may be adapted to deliver energy to the device for treatment of a patient's vasculature or to tissue surrounding the implant device 10 at the treatment site 154 for the purpose of facilitating fixation of animplant device 10, healing of tissue adjacent the device, or both. In some embodiments, energy may be delivered through a delivery apparatus 112 to the implant device 10 for treatment of a patient's vasculature, such that the implant device 10 is heated. In some embodiments, energy may be delivered via a separate elongate instrument (e.g. a catheter, not shown) to the implant device 10 for treatment of a patient's vasculature and/or surrounding tissue at the treatment site 154. Using any of the embodiments described, a method of treatment of a vascular defect, such as an aneurysm, may be done using a plurality of generally globular, spherical, or oblate spheroid devices comprising a mesh of filaments, herein called mesh devices. The mesh devices, including any suitable device for treatment of a vascular defect discussed herein, may be delivered by the methods described using any of the above-described steps.

While particular exemplary embodiments have been illustrated and described in this disclosure, it will be apparent that various modifications can be made without departing from the spirit and scope of the embodiments described herein. Accordingly, it is not intended that the scope of the disclosure be limited by the foregoing detailed description.

The invention claimed is:

1. An implant delivery system comprising:
a delivery pusher;
an implant device detachably connected to the delivery pusher by a tether having a distal portion connected to the implant device, wherein the tether is substantially non-tensioned when connecting the implant device to the delivery pusher; and
an electric coil arranged coaxially around at least a portion of the tether and comprising:
a distal winding portion with a first pitch and having a first end and a second end;
a first open-pitch winding portion extending proximally from the first end of the distal winding portion and having a second pitch that is larger than the first pitch; and
a second open-pitch winding portion extending proximally from the second end of the distal winding portion and having a third pitch that is larger than the first pitch,
wherein the electric coil is operable to achieve a temperature in the distal winding portion that is sufficient to sever the tether.

2. The implant delivery system of claim 1, wherein the first pitch is between 0.018 mm and 0.38 mm.

3. The implant delivery system of claim 2, wherein the second pitch is between 0.38 mm and 0.76 mm.

4. The implant delivery system of claim 2, wherein the third pitch is between 0.38 mm and 0.76 mm.

5. The implant delivery system of claim 1, wherein the first end of the distal winding portion is located proximally of the second end of the distal winding portion.

6. The implant delivery system of claim 1, wherein the distal winding portion has between 2 and 10 coil windings.

7. The implant deliver system of claim 1, wherein the distal winding portion has a length that is between 0.1 mm and 0.5 mm.

8. The implant delivery system of claim 1, wherein the tether is made of a material selected from a group consisting of one or more of polypropylene, polyamide, ethylene vinyl alcohol, polyethylene, polyolefin elastomer, and poly-paraphenyleneterepthalamide.

9. The implant delivery system of claim 1, wherein the implant device includes a braided vascular occlusion device.

10. The implant delivery system of claim 1, wherein the electric coil has a first resistance and is connectable to a power source by a pair of lead wires having a second resistance, and wherein the ratio of the first resistance to the second resistance is between 0.6 and 1.6.

11. The implant delivery system of claim 1, wherein the distal portion of the tether is connected to a proximal end of the implant device.

12. The implant delivery system of claim 1, wherein the electric coil has a distal end, and wherein the distal winding portion is at the distal end of the electric coil.

13. The implant delivery system of claim 1, further comprising a first small pitch winding zone extending proximally from the first open-pitch winding portion and having a fourth pitch that is smaller than the second pitch.

14. The implant delivery system of claim 13, further comprising a second small pitch winding zone extending proximally from the second open-pitch winding portion and having a fifth pitch that is smaller than the third pitch.

15. The implant delivery system of claim 14, further comprising an insulating tube disposed coaxially around the tether between the first small pitch winding zone and the second open-pitch winding portion.

16. The implant delivery system of claim 15, wherein the first small pitch winding zone is disposed over the insulation tube.

17. The implant delivery system of claim 15 wherein the first small pitch winding zone is electrically coupled to a first contact and the second small pitch winding zone is electrically coupled to a second contact, the first and second contacts being disposed on a proximal end of the delivery pusher.

18. The implant delivery system of claim 1, wherein the electric coil comprises a wire formed of a platinum-tungsten alloy.

19. The implant delivery system of claim 1, further comprising an insulating tubing extending over the electric coil.

20. The implant delivery system of claim 19, wherein a chamber is defined between the electric coil and the tether, the chamber being configured to resist the entrance of fluid.

* * * * *